United States Patent
Arakawa et al.

(10) Patent No.: US 9,139,774 B2
(45) Date of Patent: Sep. 22, 2015

(54) DIACETYLENE DERIVATIVE AND LIQUID CRYSTALLINE POLYMER HAVING DIACETYLENE STRUCTURE

(75) Inventors: Yuki Arakawa, Tokyo (JP); Gen-Ichi Konishi, Tokyo (JP); Shunpei Nakajima, Tokyo (JP); Sungmin Kang, Tokyo (JP); Junji Watanabe, Tokyo (JP); Takuya Matsumoto, Tokyo (JP); Suzushi Nishimura, Tokyo (JP); Takehiro Toyooka, Tokyo (JP)

(73) Assignees: Tokyo Institute of Technology, Tokyo (JP); JX Nippon Oil & Energy Corporation, Tokyo (JP)

( * ) Notice: Subject to any disclaimer, the term of this patent is extended or adjusted under 35 U.S.C. 154(b) by 0 days.

(21) Appl. No.: 13/985,178

(22) PCT Filed: Jan. 31, 2012

(86) PCT No.: PCT/JP2012/052114
§ 371 (c)(1),
(2), (4) Date: Aug. 13, 2013

(87) PCT Pub. No.: WO2012/111423
PCT Pub. Date: Aug. 23, 2012

(65) Prior Publication Data
US 2013/0324684 A1     Dec. 5, 2013

(30) Foreign Application Priority Data

Feb. 15, 2011 (JP) .................................. 2011-030115
Feb. 15, 2011 (JP) .................................. 2011-030116

(51) Int. Cl.
| | |
|---|---|
| *C09K 19/38* | (2006.01) |
| *C07D 213/64* | (2006.01) |
| *C07D 333/18* | (2006.01) |
| *C07D 333/54* | (2006.01) |
| *C07D 519/00* | (2006.01) |
| *C09K 19/18* | (2006.01) |
| *C09K 19/34* | (2006.01) |
| *C09K 19/04* | (2006.01) |

(52) U.S. Cl.
CPC .......... *C09K 19/3804* (2013.01); *C07D 213/64* (2013.01); *C07D 333/18* (2013.01); *C07D 333/54* (2013.01); *C07D 519/00* (2013.01); *C09K 19/18* (2013.01); *C09K 19/3444* (2013.01); *C09K 19/3491* (2013.01); *C09K 19/3809* (2013.01); *C09K 19/3823* (2013.01); *C09K 19/3852* (2013.01); *C09K 2019/0448* (2013.01); *C09K 2019/186* (2013.01)

(58) Field of Classification Search
CPC .............. C09K 19/18; C09K 19/3804; C09K 19/3444; C09K 19/3491; C09K 19/3809; C09K 19/3823; C09K 19/3852; C09K 2019/0448; C09K 2019/186; C07D 213/64; C07D 333/18; C07D 333/54; C07D 519/00

USPC ................... 349/86, 183; 428/1.1; 252/299.6; 526/256, 263, 289, 313; 546/261; 549/50, 58, 59; 568/57, 646; 560/225
See application file for complete search history.

(56) References Cited

U.S. PATENT DOCUMENTS

| | | | |
|---|---|---|---|
| 5,164,114 A | 11/1992 | Kurmeier et al. | |
| 5,338,481 A | 8/1994 | Wu et al. | |
| 2003/0072893 A1 | 4/2003 | Nakano et al. | |

FOREIGN PATENT DOCUMENTS

| | | |
|---|---|---|
| JP | H01-502831 A | 9/1989 |
| JP | H06-211704 A | 8/1994 |
| JP | H06-239786 A | 8/1994 |
| JP | H11-001445 A | 1/1999 |
| JP | 2002-308832 A | 10/2002 |
| JP | 2003-113376 A | 4/2003 |
| JP | 2004-518608 A | 6/2004 |
| WO | 0160946 A2 | 8/2001 |

OTHER PUBLICATIONS

Int'l Search Report issued Apr. 17, 2012 in Int'l Application No. PCT/JP2012/052114.
Matsumoto et al, Liquid Crystals Fundamentals & Applications, First Ed., No. 3, Kogyo Chosakai Publishing Co., p. 123 (Nov. 15, 1996).
Grant, "Diacetylenic Liquid Crystals—Synthesis and Preliminary Characterization of 4,4'-Dialkyl and 4,4'-Dialkoxy Derivatives of Diphenyldiacetylene," Mol. Cryst. Liq. Cryst., vol. 48, pp. 175-182 (1978).
Lu et al, "Synthesis and Characterization of Liquid Crystalline Monomers and Side-Chain Polymers Containing Diphenyldiacetylene Mesogens," Mol. Cryst. Liq. Cryst., vol. 225, pp. 1-14 (1993).

*Primary Examiner* — Geraldina Visconti
(74) *Attorney, Agent, or Firm* — Panitch Schwarze Belisario & Nadel LLP

(57) ABSTRACT

The present invention provides a diacetylene derivative represented by the following formula (A) which exhibits liquid crystallinity by itself and has a large refractive index anisotropy or does not exhibit liquid crystallinity by itself but exhibits a large refractive index anisotropy when added to a liquid crystalline compound:

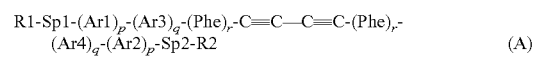

R1-Sp1-(Ar1)$_p$-(Ar3)$_q$-(Phe)$_r$-C≡C—C≡C-(Phe)$_r$-(Ar4)$_q$-(Ar2)$_p$-Sp2-R2     (A)

(wherein R1 and R2 are a hydrogen, halogen, cyano, isothiocyanate, alkyl, alkenyl, alkynyl or reactive group, SP1 and SP2 are each a spacer group, Ar1 and Ar2 are each a non-substituted or substituted aromatic carbocyclic or heterocyclic group, Ar3 and Ar4 are each a non-substituted or substituted heterocyclic group, Phe is a non-substituted or substituted 1,4-phenylene group, and p, q and r are each 0 or 1.

14 Claims, 6 Drawing Sheets

[Fig.9]
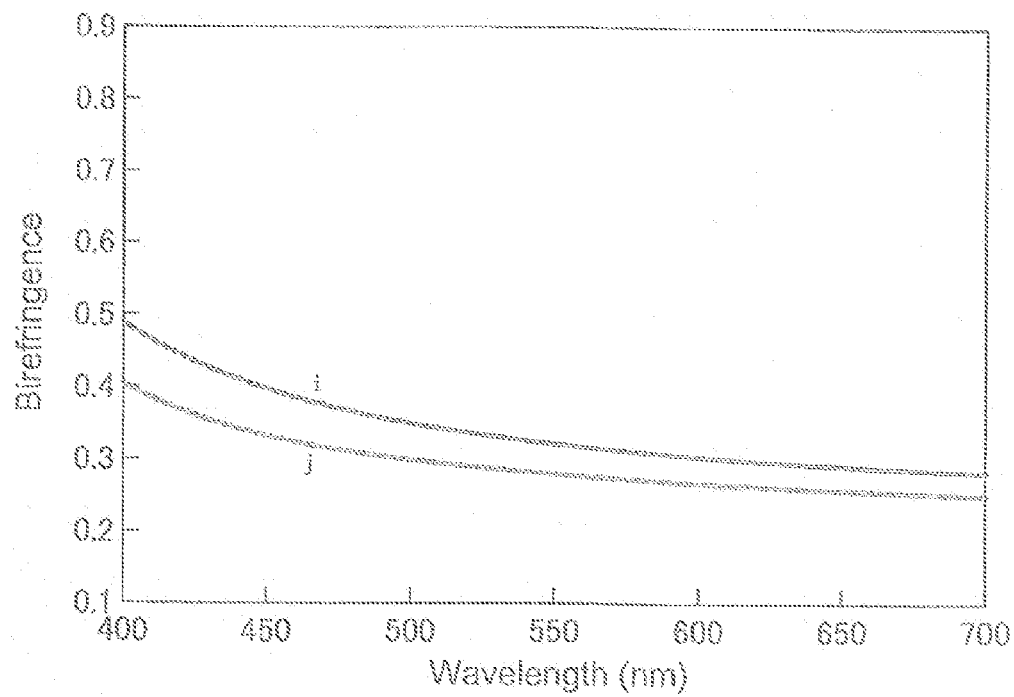
[Fig.10]
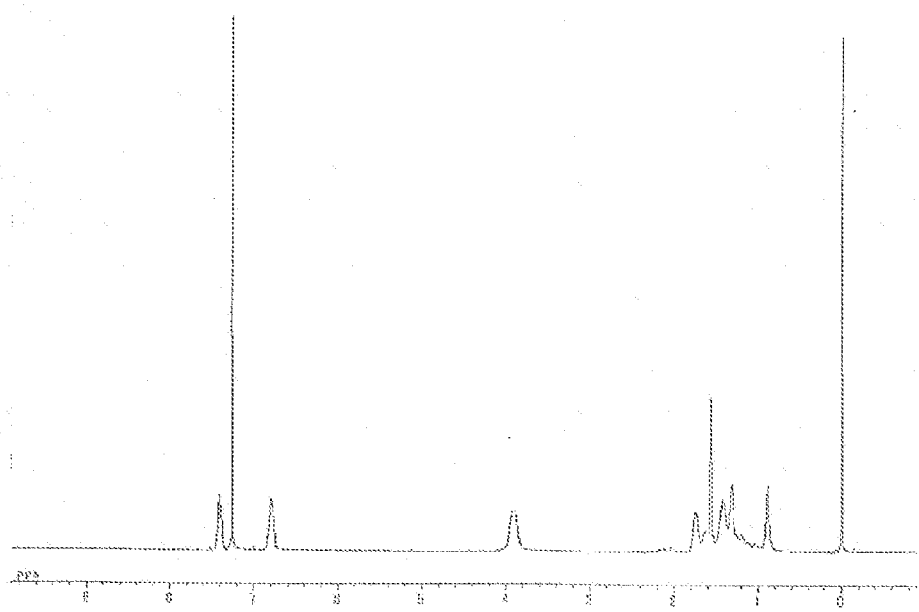

DIACETYLENE DERIVATIVE AND LIQUID CRYSTALLINE POLYMER HAVING DIACETYLENE STRUCTURE

CROSS-REFERENCE TO RELATED APPLICATION

This application is a Section 371 of International Application No. PCT/JP2012/052114, filed Jan. 31, 2012, which was published in the Japanese language on Aug. 23, 2012 under International Publication No. WO 2012/111423 A1, and the disclosure of which is incorporated herein by reference.

TECHNICAL FIELD

The present invention relates to a novel compound having a diacetylene backbone structure, a liquid crystalline composition comprising the compound, and a liquid crystalline polymer having a diacetylene structure. The present invention also relates to the use of the compound, composition or polymer in materials constituting liquid crystal display devices and optical and electron optical devices utilizing a large refractive index anisotropy.

BACKGROUND ART

In recent years, improvements in liquid crystal display device performances have become inevitable with progresses of the information-intensive society. Liquid crystalline compositions have been required to have a large refractive index anisotropy in order to improve the speed or performances of liquid crystal display devices.

Known low molecular weight liquid crystalline materials having a large refractive index anisotropy include compounds having a Schiff base or pyrimidine structure (Non-Patent Literature 1), tolan-based compounds (Patent Literatures 1 and 2), and diacetylene-based compounds (Non-Patent Literature 2, and Patent Literatures 3, 4, 5, and 6). The compounds described in these patent literatures are those with the (di)acetylene backbone having at the both ends a phenylene or naphthylene group to which an alkyl or alkoxy group bond and are described to be used as liquid crystal materials to improve the response performance of a liquid crystal display device utilizing their large refractive index anisotropy. However, although these documents disclose that the compounds have a sufficiently large refractive index anisotropy, they do not indicate the specific numeric values thereof or do not describe about the stability to heat or light.

Meanwhile, high molecular weight liquid crystalline compounds (polymers), which can be easily aligned and fixed in a liquid crystal state have been used in optical elements such as compensators or polarizers for liquid crystal display devices after being fixed in an aligned state. However, a more highly functional liquid crystalline polymer has been sought because in connection with liquid crystal display devices which have been thinner and enhanced in functions, constituting components of the devices has also been required to be enhanced in functions.

Known liquid crystalline polymers with a large refractive index anisotropy include polymers of (meth)acrylate having a tolan (acetylene) structure (Patent Literature 7). Polysiloxanes having a diacetylene backbone at a side chain and exhibiting liquid crystallinity (Non-Patent Literature 3) are also known, but they have a high melting point and thus cannot be sufficient in forming processability.

CITATION LIST

Patent Literature

[Patent Literature 1] Japanese Patent Application Laid-Open Publication No. 01-502831
[Patent Literature 2] Japanese Patent Application Laid-Open Publication No. 06-239786
[Patent Literature 3] Japanese Patent Application Laid-Open Publication No. 11-001445
[Patent Literature 4] Japanese Patent Application Laid-Open Publication No. 06-211704
[Patent Literature 5] U.S. Pat. No. 5,338,481
[Patent Literature 6] Japanese Patent Application Laid-Open Publication No. 2004-518608
[Patent Literature 7] Japanese Patent Application Laid-open Publication No. 2002-308832

Non-Patent Literature

[Non-Patent Literature 1] "Liquid Crystals Fundamentals & Applications" first edition, third issue, page 123, by Shouichi Matsumoto, Ichiro Tsunoda, published by Kogyo Chosakai Publishing Co., Ltd., Nov. 15, 1996
[Non-Patent Literature 2] "Mol. Cryst. Liq. Cryst." vol. 48, 175-182 by B. Grant, 1978,
[Non-Patent Literature 3] "Mol. Cryst. Liq. Cryst." vol. 225, 1-14 by Yong-Hong Lu, Chain-Shu Hsu, Shin-Tson Wu, 1993

SUMMARY OF INVENTION

Technical Problem

The present invention has an object to provide a compound exhibiting liquid crystallinity and having a large refractive index anisotropy by itself, a compound not exhibiting liquid crystallinity but exhibiting a large refractive index anisotropy by itself when added to a liquid crystalline compound, and a liquid crystalline composition and polymer produced using any of such compounds, which can solve the above-described problems as well as a liquid crystal device or optical device having excellent properties.

Solution to Problem

As the result of extensive studies by the inventors of the present invention in order to achieve the object, the present invention has accomplished on the basis of the finding that a novel diacetylene compound having a diacetylene (1,3-butadiyne) backbone was able to achieve the above-described object.

That is, the present inventions are as follows:
[1] a diacetylene derivative represented by the following formula (A)

$$\text{R1-Sp1-(Ar1)}_p\text{-(Ar3)}_q\text{-(Phe)}_r\text{-C} \equiv \text{C--C} \equiv \text{C-(Phe)}_r\text{-(Ar4)}_q\text{-(Ar2)}_p\text{-Sp2-R2} \quad (A)$$

wherein R1 and R2 are each independently hydrogen, halogen, cyano, isothiocyanate, alkyl having 1 to 15 carbon atoms, which is not substituted or is monosubstituted or polysubstituted with halogen, cyano, trifluoromethyl or a reactive group, alkenyl or alkynyl having 2 to 15 carbon atoms, which is not substituted or is monosubstituted or polysubstituted with halogen, cyano, trifluoromethyl or a reactive group, or a reactive group, wherein one or more non-adjacent —CH$_2$— groups may be substituted with —O—, —CO—, —COO— and/or —OCO—, Sp1 and Sp2 are each independently —O—, —S—, —CO—, —COO—, —OCO—, —OCO—O—, —CO—NR3-, —NR3-CO—, —O(CH$_2$)$_n$—, —(CH$_2$)$_n$O—, —CH=CH—COO—, —OCO—CH=CH—, —(CH$_2$)$_m$—, —(SiR4R5-O)$_n$— or a single bond, where m and n are each independently an integer of 1 to 10, R3, R4 and R5 are each independently hydrogen or alkyl having 1 to 4 carbon atoms, Ar1 and Ar2 are each independently an aromatic carbocyclic or heterocyclic group having up to 16 carbon atoms, which is not substituted or is mono-substituted or polysubstituted with halogen, cyano, trifluoromethyl, methyl, ethyl, methoxy or ethoxy and may include a condensed ring, Ar3 and Ar4 are each independently a heterocyclic group having up to 16 carbon atoms, which is not substituted or is monosubstituted or polysubstituted with halogen, cyano, trifluoromethyl, methyl, ethyl, methoxy or ethoxy and may include a condensed ring or be a plurality of heterocyclic groups connected via single bonds, Phe is 1,4-phenylene, which is not substituted or is monosubstituted or polysubstituted with halogen, cyano, trifluoromethyl, methyl, ethyl, methoxy or ethoxy, and p, q and r are each an integer of 0 or 1.

[2] the diacetylene derivative according to [1] above where the compound represented by formula (A) is a compound represented by formula (1):

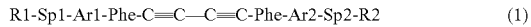

R1-Sp1-Ar1-Phe-C≡C—C≡C-Phe-Ar2-Sp2-R2    (1)

[3] the diacetylene derivative according to [1] above where the compound represented by formula (A) is a compound represented by formula (2);

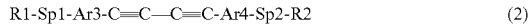

R1-Sp1-Ar3-C≡C—C≡C-Ar4-Sp2-R2    (2)

[4] the diacetylene derivative according to [1] above where the compound represented by formula (A) is a compound represented by formula (3);

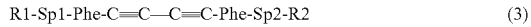

R1-Sp1-Phe-C≡C—C≡C-Phe-Sp2-R2    (3)

[5] the diacetylene derivative according to [1] to [4] above where the reactive group is hydroxyl, carboxyl, acid anhydride, maleimide, vinyloxy, oxiranyl, oxetanyl, vinyl, (meth)acrylate, or silyl;

[6] the diacetylene derivative according to [1] or [2] above where Ar1 and Ar2 are each furane-2,5-diyl, thiophene-2,5-diyl, pyrrole-2,5-diyl, 1,4-phenylene, naphthalene-2,6-diyl, pyridine-2,5-diyl, pyrimidine-2,5-diyl, or indane-2,5-diyl;

[7] the diacetylene derivative according to [1] or [3] above where Ar3 and Ar4 are each furane-2,5-diyl, thiophene-2,5-diyl, pyrrole-2,5-diyl, pyridine-2,5-diyl, or pyrimidine-2,5-diyl;

[8] a liquid crystalline composition containing one or more types of diacetylene derivative according to any of [1] to [7] above;

[9] the diacetylene derivative according to any of [1] to [7] above where it is used for optics or electrooptics;

[10] the liquid crystalline composition according to [8] above where it is used for optics or electrooptics;

[11] a liquid crystalline polymer having a diacetylene structure produced by reacting the diacetylene derivative of any of [1] to [7] above (provided that in the compound represented by formula (A), at least one of R1 and R2 is a group having a reactive group);

[12] a liquid crystalline polymer composition containing the liquid crystalline polymer having the diacetylene structure of [11] above; and

[13] the liquid crystalline polymer according to [11] above where it is used for optics or electrooptics.

Advantageous Effects of Invention

The diacetylene derivative of the present invention exhibits a large refractive index anisotropy regardless of whether or not it has liquid crystallinity and thus is useful as a material constituting optical and electrooptical devices such as liquid crystal display devices. The liquid crystalline polymer having the diacetylene structure of the present invention has a large refractive index anisotropy and easy in forming into a film, which can be used for optical and electrooptical devices, such as a polarizer, a compensator, or a beam splitter.

BRIEF DESCRIPTION OF THE DRAWINGS

FIG. 9 is a graph showing the wavelength dependence of birefringence of a liquid crystalline composition comprising the diacetylene derivative obtained in Example 8 and (4-hexyloxyphenyl-1-yl)buta-1,3-diyne, wherein the lines i and j indicate the birefringences of the composition and (4-hexyloxyphenyl-1-yl) buta-1,3-diyne, respectively;

FIG. 10 is a graph showing the $^1$H-NMR spectrum of the polymer produced in Example 9;

DESCRIPTION OF EMBODIMENT

Figure 1:
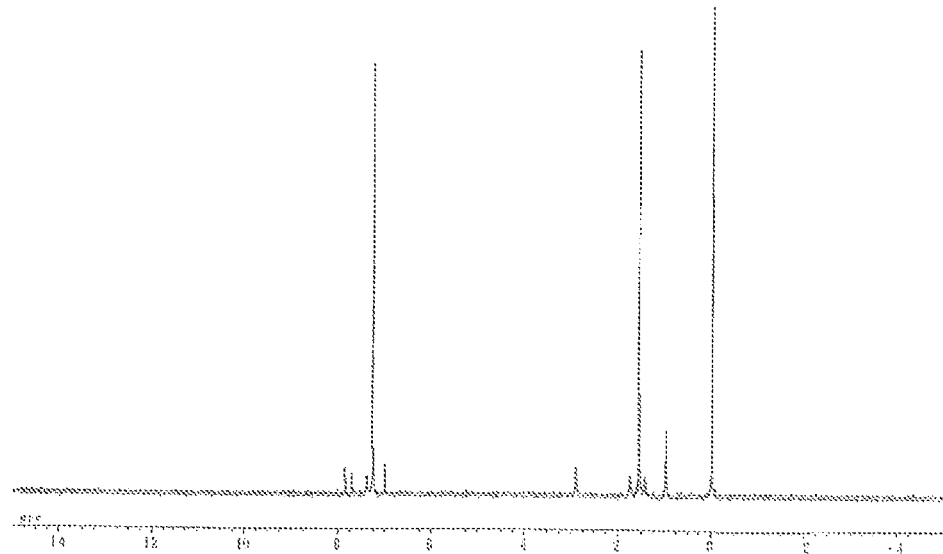
FIG. 1 is a graph showing the $^1$H-NMR spectrum of the diacetylene derivative produced in Example 1.

The present invention will be described below.
The present invention is a diacetylene derivative represented by the following formula (A):

R1-Sp1-(Ar1)$_p$-(Ar3)$_q$-(Phe)$_r$-C≡C—C≡C-(phe)$_r$-(Ar4)$_q$-(Ar2)$_p$-Sp2-R2   (A).

The diacetylene derivative represented by formula (A) of the present invention is a compound where substituents R1 and R2 bond to the diacetylene(1,3-butadiyne) backbone via a carbocyclic group or heterocyclic group, such as phenylene and spacer groups Sp1 and Sp2 and is preferably a compound represented by any of formulas (1) to (3):

R1-Sp1-Ar1-Phe-C≡C—C≡C-Phe-Ar2-Sp2-R2   (1)

R1-Sp1-Ar3-C≡C—C≡C-Ar4-Sp2-R2   (2)

R1-Sp1-Phe-C≡C—C≡C-Phe-Sp2-R2   (3)

The 1,3-butadiyne backbone part is a feature of the compounds of formulas (A) and (1) to (3) of the present invention. These compounds have surprisingly high chemical and thermal stabilities. In general, these compounds exhibit a high anisotropy and a nematic liquid crystallinity and/or smectic liquid crystallinity correspondingly to their structures.

In formulas (A) and (1) to (3), R1 and R2 are each independently hydrogen, halogen, cyano, isothiocyanate, alkyl having 1 to 15 carbon atoms, which is not substituted or is monosubstituted or polysubstituted with halogen, cyano, trifluoromethyl or a reactive group, alkenyl or alkynyl group having 2 to 15 carbon atoms, which is not substituted or is monosubstituted or polysubstituted with halogen, cyano, trifluoromethyl or a reactive group, or a reactive group, wherein one or more non-adjacent —CH$_2$— groups may be substituted with —O—, —CO—, —COO— and/or —OCO—.

Specific examples include methyl, ethyl, propyl, butyl, pentyl, hexyl, heptyl, octyl, nonyl, decyl, undecyl, dodecyl, ethenyl, propenyl, butenyl, pentenyl, hexenyl, heptenyl, octenyl, nonenyl, decenyl, undecenyl, dodecenyl, propynyl, butynyl, pentynyl, hexynyl, heptynyl, octynyl, nonynyl, decynyl, dodecynyl, ethyny, propenyl, butenyl, pentenyl, hexenyl, heptenyl, octenyl, nonenyl, decenyl, undecenyl, dodecenyl, 2-methylpropyl, 2-methylbutyl, 3-methylbutyl, 3-methylpentyl, 2-methylhexyl, 2-methyldecyl, 2-fluoroethyl, 3-fluoropropyl, 4-fluorobutyl, 6-fluorohexyl, 4,4-difluorobutyl, 6,6-difluorohexyl, 2-chloroethyl, 3-chloropropyl, 4-chlorobutyl, 6-chlorohexyl, perfluoroethyl, perfluorobutyl, 1-cyanoethyl, 1-cyanobutyl, 2-cyanobutyl, 1-trifluoromethylethyl, 1-trifluoromethylbutyl, methoxy, ethoxy, butyloxy, pentyloxy, hexyloxy, octyloxy, decyloxy, dodecyloxy, trifluoromethoxy, 2-fluorobutyloxy, 2-fluorohexyloxy, 2-fluorobutyloxycarbonyl, groups where the reactive group described below bond to these groups, hydrogen, fluorine, trifluoromethyl, cyano, isothiocyanate and a reactive group.

In formulas (A) and (1), Ar1 and Ar2 are each independently an aromatic carbocyclic or heterocyclic group having up to 16 carbon atoms, which is not substituted or is monosubstituted or polysubstituted with halogen, cyano, trifluoromethyl, methyl, ethyl, methoxy or ethoxy and may include a condensed ring. Preferably, Ar1 and Ar2 are each an aromatic group, a 5-membered or 6-membered heterocyclic group, or a group containing the 5-membered ring or 6-membered ring of two or three condensed aromatic rings or heterocyclic rings, and these rings may contain two or more hetero atoms, particularly hetero atoms selected from N, O and S. All of these groups may not be substituted or may be monosubstituted or polysubstituted with F, Cl, CN, OH, NO$_2$, CH$_3$, C$_2$H$_5$, OCH$_3$, OC$_2$H$_5$, COCH$_3$, COC$_2$H$_5$, COOCH$_3$, COOC$_2$H$_5$, CF$_3$, OCF$_3$, OCHF$_2$ or OC$_2$F$_5$. Particularly preferred are F, Cl, CN, CH$_3$, C$_2$H$_5$, OCH$_3$, and OCF$_3$.

Preferred groups for Ar1 and Ar2 include furane, pyrrole, thiophene, oxazole, thiazole, thiadiazole, imidazole, phenylene, pyridine, pyrimidine, pyrazine, indane, naphthalene, tetrahydronaphthalene, anthracene and phenanthrene.

Particularly preferred for Ar1 and Ar2 include furane-2,5-diyl, thiophene-2,5-diyl, pyrrole-2,5-diyl, 1,4-phenylene, pyridine-2,5-diyl, pyrimidine-2,5-diyl, naphthalene-2,6-diyl, 1,2,3,4-tetrahydronaphthalene-2,6-diyl, and indane-2,5-diyl.

In formulas (A), (1) and (3), Phe is a 1,4-phenylene group, which is not substituted or is monosubstituted or polysubstituted with halogen, cyano, trifluoromethyl, methyl, ethyl, methoxy or ethoxy. Examples of Phe include 1,4-phenylene, 2-fluoro-1,4-phenylene, 3-fluoro-1,4-phenylene, 2,3-difluoro-1,4-phenylene, 2-chloro-1,4-phenylene, 2-cyano-1,4-phenylene, 2-methyl-1,4-phenylene, and 3-methyl-1,4-phenylene groups.

In formulas (A) and (2), Ar3 and Ar4 are each independently a heterocyclic group having up to 16 carbon atoms, which is not substituted or is monosubstituted or polysubstituted with halogen, cyano, trifluoromethyl, methyl, ethyl, methoxy or ethoxy and may include a condensed ring and may be a plurality of heterocyclic groups connected via single bonds. Preferably, Ar3 and Ar4 are each a 5-membered or 6-membered heterocyclic group or a group containing two or three condensed rings containing a heterocyclic group. The atom constituting the heterocyclic group is one or more hetero atom, particularly preferably a hetero atom selected from N, O and S. All of these groups may not be substituted or may be monosubstituted or polysubstituted with F, Cl, CN, OH, NO$_2$, CH$_3$, C$_2$H$_5$, OCH$_3$, OC$_2$H$_5$, COCH$_3$, COC$_2$H$_5$, COOCH$_3$, COOC$_2$H$_5$, CF$_3$, OCF$_3$, OCHF$_2$ or OC$_2$F$_5$. Particularly preferred are F, Cl, CN, CH$_3$, C$_2$H$_5$, OCH$_3$, and OCF$_3$.

Preferred examples of the groups for Ar3 and Ar4 include groups derived from furane, pyrrole, thiophene, oxazole, thiazole, thiadiazole, imidazole, pyridine, pyrimidine, and pyrazine. Particularly preferred Ar3 and Ar4 include furane-2,5-diyl, thiophene-2,5-diyl, pyrrole-2,5-diyl, pyridine-2,5-diyl, and pyrimidine-2,5-diyl.

Sp1 and Sp2 are groups also referred to as "spacer" and may be all groups that are known by a person skilled in the art to be used for this purpose.

Sp1 and Sp2 are each independently —O—, —S—, —CO—, —COO—, —OCO—, —OCO—O—, —CO—NR$_3$—, —NR$_3$—CO—, —O(CH$_2$)n-, —(CH$_2$)$_n$O—, —CH═CH—COO—, —OCO—CH═CH—, —(CH$_2$)$_m$—, —(SiR4R5-O)$_n$— or a single bond, where m and n are each independently an integer of 1 to 10 and R3, R4 and R5 are each hydrogen or an alkyl group having 1 to 4 carbon atoms.

Preferred spacers include ethylene, propylene, butylene, pentylene, hexylene, heptylene, octylene, nonylene, decylene, undecylene, dodecylene, octadecylene, ethyleneoxy ethylene, methyleneoxy butylene, ethylene-N-methyl-iminoethylene, ethenylene, propenylene and butenylene.

The above-mentioned reactive group is a group that can form a polymer under appropriate selected reaction conditions and may be hydroxyl, carboxyl, acid anhydride, maleimide, vinyl, vinyloxy, oxiranyl, oxetanyl, (meth)acrylate, and silyl groups, among which preferred are groups that are easily polymerized or condensed, and preferably selected from CH$_2$═CW$^1$—COO—,

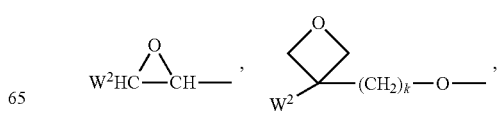

$CH_2=CW^2-(O)k1-$, $CH_3-CH=CH-O-$, $(CH_2=CH)_2CH-OCO-$, $(CH_2=CH-CH_2)_2CH-OCO-$, $(CH_2=CH)_2CH-O-$, $(CH_2=CH-CH_2)_2N-$, $HO-CW^2W^3-$, $HS-CW^2W^3-$, $HW^2N-$, $HO-CW^2W^3-NH-$, $CH_2=CW^1-CO-NH-$, $CH_2=CH-(COO)k1-Phe-(O)k2-$, $Ph-CH=CH-$, $HOOC-$, $OCN-$ and $W^4W^5W^6Si$.

In these formulas, $W^1$ is H, Cl, CN, phenyl or an alkyl group having 1 to 5 carbon atoms, particularly H, Cl or $CH_3$, $W^2$ and $W^3$ are each independently H or an alkyl group having 1 to 5 carbon atoms, particularly methyl, ethyl or n-propyl, $W^4$, $W^5$ and $W^6$ are each independently Cl, or an oxaalkyl or oxacarbonylalkyl group having 1 to 5 carbon atoms, Ph is phenyl, Phe is 1,4-phenylene, k is an integer of 0, 1 or 2, and $k^1$ and $k^2$ are each independently an integer of 0 or 1. Particularly preferred reactive groups are vinyl, (meth)acrylate, oxiranyl and oxetanyl groups, and most preferred is a (meth) acrylate group.

Next, a method for synthesizing the diacetylene derivatives represented by formulas (1) to (3) will be described.

The compounds represented by formulas (1) to (3) per se can be produced with a known very simple method. For example, they can be synthesized by the method described in "Methoden der Organischen Chemie" by Houben-Weyl, Thime-Verlag, Stuttgart, which is a standard academic book of the organic chemistry or a similar method thereto. More specifically, as described in "Preparative Acetylenic Chemistry" 2nd Ed. by L. Brandsma, Elsevier, Amsterdam NL, (1988) or "Advances in Organic Chemistry" Vol. 4, by Cadiot-Chodkiewicz (G. Eglinton, W. Mc Grae in Raphael, Taylor and Wynberg(eds) Interscience publishers, N.Y. (1963), in the presence of copper complex, they can be produced by coupling a terminal alkyne with a haloalkyne derivative.

The terminal alkynes and haloalkynes, which are needed for each other to be coupled are known or similar to known compounds and can be produced per se by a conventional method. For example, aldehyde can be converted to a necessary alkyne by the Wittig reaction using $CBr_4/PPh_3$ and an elimination reaction. If necessary, the alkynes can be converted from the corresponding haloalkene by a conventional method, metallization and halogenation. When R1 or R2 is chiral, the derivative of the present invention can be used a chiral additive (dopant).

When a reactive group is introduced, a reaction of a compound bonding the reactive group with a compound having a diacetylene group or coupling of an acetylene compound bonding the reactive group with a different acetylene compound may be carried out to an extent that synthesis of the intended compound having a diacetylene group is not bothered.

The diacetylene derivative of the present invention thus produced may not exhibit liquid crystallinity alone, but when it exhibits liquid crystallinity, it varies in liquid crystalline phase behavior (phase transition temperature) or refractive index anisotropy (birefringence) depending on the groups introduced in the derivative or the whole structure thereof. However, the diacetylene derivative exhibits a birefringence Δn (measured at 550 nm) of preferably 0.25 or higher, particularly preferably 0.30 or higher when measured at the liquid crystalline temperature which is 10° C. lower than the isotropic phase transition temperature (Ti° C.).

The liquid crystalline composition of the present invention is a liquid crystalline composition having at least one type of the diacetylene derivatives represented by formulas of (1) to (3). The other components constituting the composition may be compounds represented by formulas (1) to (3) that are different from that representing the one type of derivative and thus are not particularly restricted but are preferably compound exhibiting a liquid crystalline phase.

The compounds of formulas (1) to (3) largely contribute to the optical anisotropy of the composition. The mixed ratio of the compounds of formulas (1) to (3) may be changed on a wide range depending on the requisite performances of the liquid crystalline composition and thus cannot be necessarily determined. However, it is usually from 0.1 to 100 percent by mass, preferably from 1 to 80 percent by mass.

As described above, the liquid crystalline composition of the present invention is a composition containing at least one type of the diacetylene derivatives of the present invention, and other components constituting the composition are preferably those exhibit a nematic liquid crystalline phase.

The diacetylene derivatives represented by formulas (1) to (3) of the present invention are excellent in miscibility with other liquid crystalline compounds and thus can be mixed appropriately depending on requisite performances for a liquid crystal cell so as to improve the performances thereof.

Other components constituting the composition are preferably those exhibiting a nematic phase, such as azoxybenzenes, benzylidene-anilines, biphenyls, terphenyls, phenyl benzoate or cyclohexylesters, phenyl ester or cyclohexyl esters of cyclohexanecarboxylic acid, phenyl esters or cyclohexyl esters of cyclohexylbenzoic acid, phenyl ester or cyclohexyl esters of cyclohexylcyclohexanecarboxylic acid, cyclohexylphenyl esters of benzoic acid, cyclohexanecarboxylic acid and cyclohexylcyclohexanecarboxylic acid, phenylcyclohexanes, cyclohexyl biphenyls, phenyl cyclohexylcyclohexanes, cyclohexylcyclohexanes, cyclohexylcyclohexenes, cyclohexylcyclohexylcyclohexenes, 1,4-bis-cyclohexylbenzenes, 4,4'-bis-cyclohexyl biphenyls, phenyl- or cyclohexyl-pyrimidines, phenyl- or cyclohexyl-pyridines, phenyl- or cyclohexyl-pyridazines, phenyl- or cyclohexyl-dioxanes, phenyl- or cyclohexyl-1,3-dithianes, 1,2-diphenyl-ethanes, 1,2-dicyclohexylethanes, 1-phenyl-2-cyclohexylethanes, 1-cyclohexyl-2-(4-phenylcyclohexyl)-ethanes, 1-cyclohexyl-2-biphenyl-ethanes, 1-phenyl-2-cyclohexylphenylethanes, halogenated stilbenes, benzylphenyl ether, tolans, and mixtures thereof.

The compound represented by formulas (1) to (3) and/or liquid crystalline composition of the present invention can be used in optics or electrooptics. For example, the compound and/or liquid crystalline composition can be used in liquid crystal mixtures for various displays such as a TN or STN display, an IPS (In Plane Switching) display, a display of a VA (Vertical Aligned) mode such as VAN (Vertical Aligned Nematic) or VAC (Vertical Aligned Cholesteric) mode, an ECB (Electrically Controlled Birefringence) display, a display of a DAP (Deformation of Aligned Phase), CSH (Color Super Homeotropic) or ASM (Axisymmetric Micro-cell) mode, a phase-change mode display, a guest-host mode display, a flexoelectric display, a ferroelectric display, a bistable nematic display and a cholesteric display such as a PSCT (Polymer Stabilized Cholesteric Textured) display, and a PDLC, polymer gel or polymer network display.

The liquid crystalline composition and electric-optical devices (liquid crystal display device) may be produced with conventional methods.

The present invention also relates to a liquid crystalline polymer having a diacetylene structure resulting from a reaction of the above-described diacetylene derivative. However, in the compound represented by formula (A), at least one of R1 and R2 is necessarily a group having a reactive group.

The liquid crystalline polymer having a diacetylene structure of the present invention may be produced by reacting the reactive groups in formulas (1) to (3) under conditions suitable for the reaction thereof. No particular limitation is imposed on the reaction conditions. For example, when the compound has a polymerizable group, anionic polymerization, cationic polymerization or radical polymerization may be carried out depending on the reactivity of the polymerizable group. When the compound has a different reactive group such as a hydroxyl or carboxyl group, condensation such as esterification or addition (hydrosilylation) of a carbon-carbon double bond to a hydrogen-silicon bond can easily produce the liquid crystalline polymer.

The compounds having a reactive group represented by formulas (1) to (3) may be blended with various additives such as an anti-oxidant, an ultraviolet absorber and a light stabilizer so as to improve the storage stability. Other additives such as a chain transfer agent, a copolymerizable compound (reactive diluent or the like), a surface active agent, a flow improver, an anti-foaming agent, a dye, and a pigment may be added to an extent that the resulting polymer is not prohibited from exhibiting liquid crystallinity.

The above-mentioned polymerization is preferably carried out in a solvent that can dissolve the compound and represented by formulas (1) to (3) and the polymer produced therefrom. Examples of such a solvent include hexane, heptane, octane, decane, cyclohexane, decahydronaphthalene, benzene, toluene, xylene, mesitylene, methyl isobutyl ketone, tetrahydrofuran, cyclohexanone, N-methyl-2-pyrrolidinone, γ-butyrolactone, acetic acid ethyl, lactic acid ethyl, benzoic acid ethyl, dimethylformamide, dimethylacetamide, ethylene glycol dimethyl ether, diethylene glycol dimethyl ether, ethanol, propanol, butoxy ethanol, hexyloxy ethanol, chloroform, chlorobenzene, and mixtures thereof. The resulting polymer may be recovered by for example vacuum distillation of the solvent or reprecipitation in a poor solvent such as methanol.

The polymerization may be photo-polymerization. The method and conditions for the photo-polymerization may be selected from the conventional ones. Examples of the light to be used include ultraviolet, infrared, visible light, and X-ray. For example, in the case of using ultraviolet while a composition blended with 0.05 to 20 percent by mass, preferably 0.2 to 10 percent by mass of a photo-polymerization initiator suitable for the wavelength of ultraviolet to be emitted substantially in the absence of oxygen or moisture or the compound of any of formulas (1) to (3) is coated over a substrate having alignability or sandwiched between a pair of substrates, the composition may be irradiated with the ultraviolet from an appropriate light source. The amount of the photo-polymerization initiator deviating the above range is not preferred because it remains after photo-polymerization and is likely to be colored.

Examples of the photo-polymerization initiator include benzoin ethers, benzophenones, acetophenones, benzyl ketals, acylphosphine oxides, trihalomethyl triazines, aromatic iodonium salts, aromatic sulfonium salts, aromatic phosphonium salts, and diazodisulfone compounds.

The irradiance level of ultraviolet varies depending on the formulation of the composition or irradiation temperature but is from 10 $mJ/cm^2$ to 2 $J/cm^2$, preferably 50 $mJ/cm^2$ to 1 $J/cm^2$. The amount deviating this range is not preferred because the polymerization progresses insufficiently or the resulting product likely degrades due to excessive exposure.

No particular limitation is imposed on the ultraviolet source if it can generate ultraviolet in a large level. Examples of the source include a low pressure mercury lamp, a high pressure mercury lamp, an ultra-high pressure mercury lamp, a metal halide lamp, a carbon arc lamp, and an electrodeless discharge lamp.

The liquid crystalline polymer of the present invention thus produced varies in liquid crystalline phase behavior (phase transition temperature) or optical anisotropy (birefringence) depending on the compounds represented by formulas (1) to (3) to be a monomer or the molecular weight but is preferably 0.20 or greater, particularly preferably 0.25 or greater in birefringence $\Delta n$ (measured at 550 nm) in its liquid crystalline phase state.

No particular limitation is imposed on the molecular weight of the liquid crystalline polymer of the present invention. However, the number average molecular weight is usually from 2000 to 500000, preferably from 3000 to 50000. The molecular weight outside the range is not preferred because the shaped product produced from the polymer would be fragile or it would be difficult for the polymer to exhibit a sufficient liquid crystal phase.

The liquid crystalline polymer of the present invention may be usually used as an optical element such as a retardation film in the form of film utilizing the optical anisotropy. The polymer is preferably formed into a film by being heated and melted over a substrate having alignability or by being dissolved in a suitable solvent that can dissolve the polymer, such as hexane, heptane, octane, decane, cyclohexane, decahydronaphthalene, benzene, toluene, xylene, mesitylene, methyl isobutyl ketone, tetrahydrofuran, cyclohexanone, N-methyl-2-pyrrolidinone, γ-butyrolactone, acetic acid ethyl, lactic acid ethyl, benzoic acid ethyl, dimethylformamide, dimethylacetamide, ethylene glycol dimethyl ether, diethylene glycol dimethyl ether, ethanol, propanol, butoxy ethanol, hexyloxy ethanol, chloroform, chlorobenzene, and mixtures thereof. The used solvent is preferably removed by drying, and examples of the drying method include natural drying, drying by heating, drying under reduced pressure, and heating under reduced pressure.

In the above-described photo-polymerization, when the compound of any of formulas (1) to (3) that is a monomer exhibits liquid crystallinity, the compound may be polymerized while it is retained in a liquid crystal alignment and fixed into the aligned state.

In the case of using a solution, it may be coated using an appropriate device such as a spin coater, a bar coater, a roll coater or a die coater. Examples of the above-mentioned substrate having alignability include plastic films formed from polyethylene terephthalate, polyethylene naphthalate, triacetyl cellulose, norbornene resin, polyimide, polycarbonate, polysulfone, polyethersulfone, poly etherether keton, polyarylate, polyvinyl alcohol, and polyphenylene sulfide, glass plates, and micro-groove structured metal plates or foils of iron, copper and aluminum, all of which may be subjected to an alignment treatment such as aligning film-coating, rubbing, oblique vapor deposition, stretching, or photo-alignment if necessary. The substrates may be in the form of sheet or elongate film.

The resulting film is preferably heated so as to be aligned sufficiently. The heating temperature may be arbitrarily set based on the liquid crystalline temperature range of the liquid crystalline polymer to be used or the heat resistance of the substrate. The polymer is usually aligned in the temperature range where the polymer forms a liquid crystalline phase, for example the nematic phase transition temperature or higher and lower than the isotropic phase transition temperature. Alternatively, the polymer may be aligned in an intended form by heating a liquid crystalline polymer to a temperature which is the isotropic phase temperature or higher to be in an isotropic phase and then adjusting the cooling rate. Although the period for the alignment treatment may be arbitrarily determined, it is usually from 10 seconds to 30 minutes. For melting and coating the solution, various additives such as an anti-oxidant to improve the stability or uniformity of the film, an ultraviolet absorber or light stabilizer, and a surface active agent or an anti-foaming agent to improve the wettability may be added to an extent that the present invention is not hindered from achieving the purposes. The amounts of these additives may be arbitrarily selected from the ranges where they are generally used. Alternatively, various compounds having an optical active group that are miscible regardless of whether they have liquid crystallinity or not may be added in order to form a cholesteric alignment.

The thickness of the film varies depending on its applications but is usually from 0.05 μm to 50 μm, preferably 0.1 μm to 20 μm. The thickness deviating this range is not preferred because the uniformity of the thickness would degrade or the film would be aligned insufficiently.

In the case where the above-described substrate having alignability is not optically preferred because it is colored or opaque, the film having been heat-aligned may be transferred via a tacky adhesive or adhesive to a different substrate suitable for the application.

No particular limitation is imposed on the tacky adhesive or adhesive used for transferring (hereinafter collectively referred to as "tacky/adhesive") if it is of an optical grade having an adequate adhesivity to the both interface to be attached. Examples of the tacky/adhesive include acrylic-, epoxy resin-, ethylene-vinyl acetate copolymer-, rubber-, urethane-based adhesives, mixture types thereof, or various reactive adhesives of such as thermal curing type and/or photo curing type or electron radiation curing types. The photo curing type is preferred because it is easily treated.

The photo curing type acrylic tacky/adhesive may be any of commercially available ultraviolet (UV) curing type tacky/adhesives and those suitably modified depending on the adhesivity of a liquid crystalline composition.

The acrylic tacky/adhesive may be prepared by adding various types of commercially available (meth)acrylic monofunctional monomers and polyfunctional monomers, oligomers such as polyester(meth)acrylates and polyurethane (meth)acrylates, and additives such as photo-polymerization initiators, viscosity modifier (thickener), surface active agents and dispersants.

Before transferring, a surface treatment such as corona discharge treatment, ultraviolet irradiation treatment or flame treatment may be carried out on a surface to be applied with a tacky/adhesive so as to improve the adhesivity.

Furthermore, (fine) particles having a different refractive index from the acrylic tacky/adhesive may be added to diffuse or scatter light. Examples of materials for the (fine) particles include silica, alumina, ITO, silver and various (cross-linked) plastics. The tacky adhesive layer may contain additives that are often added thereto such as natural or synthetic resins, in particular fillers or pigments containing tackiness-imparting resins, glass fibers, glass beads, metal powders, and other inorganic powders, dyes, anti-oxidants. The amount of these additives varies depending on the types, constituting components and functions but is usually preferably from 0.01 percent by mass to 20 percent by mass on the basis of the acrylic tacky/adhesive.

The different substrates mentioned above may be any of conventional substrates without any limitation. Examples of such substrates include films of resins such as polycarbonate, norbornene resin, triacetylcellulose, acryl, maleimide and styrene and films produced by stretching these films, polyvinyl alcohol-based polarizers and reflection type polarizers of a laminate of a plurality of resin films with different refractive indexes.

The resulting film may be used as an optical film, a polarizer, a compensator or a reflection film. When the film is used as a compensator of a liquid crystal display device, examples thereof include those of TN (twisted nematic) type, STN (super twisted nematic) type, IPS (In Plane Switching) type, VA (vertical aligned) type, ECB (electrically controlled birefringence) type, and ASM (Axisymmetric Micro-cell) type.

The liquid crystalline polymer of the present invention may be used as a composition for a PDLC display or a polymer gel or polymer network display.

The liquid crystalline polymer composition and electric-optical device (liquid crystal cell) may be produced by any conventional method.

EXAMPLES

The present invention will be further described in the following examples and comparative examples, but the present invention should not be construed as being limited thereto. Each method used for measurements will be described.

1. Measurement of Birefringence

The following instruments were used for the measurement.

Polarizing microscope: ECLIPSE LV 100 POL, manufactured by Nikon Corporation

Optical fiber: BIF600-VIS-NIR, manufactured by Ocean Optics, Inc.

Spectroscope: USB4000, manufactured by Ocean Optics, Inc.

Liquid crystal cell used for evaluation: KSRP-03/B311P1NSSO$_5$, manufactured by EHC KK The birefringence was measured at a liquid crystalline phase temperature that is 10° C. lower than the isotropic phase transition temperature at a wavelength of 400 to 1000 nm to measure the spectrum in accordance with the following procedures.

(1) Measurement of Cell Gap

A cell without a liquid crystal was irradiated from the below with light to measure the transmitted interference light so that the air layer thickness was determined (formula (1) below) and defined as the cell gap.

$$2d = m\lambda \quad (1)$$

(2) Microspectroscopic Analysis

Liquid crystal was enclosed in the cell with a cell gap d determined by the above (1) and aligned homogeneously so as to produce a birefringence body. The birefringence body was sandwiched between a pair of polarizers each having a polarizing axis crossing to one another to measure the spectral transmittance. The wavelengths at which the spectral transmittance of the body were maximum and minimum (formula (2) below) and the retardations of the body at each of the wavelengths (formula (3)) were fitted with Cauchy's dispersion formula developed to the fourth-order (formula (4)) so as to determine the birefringence index Δn and wavelength dispersion of retardation R of the birefringence body.

$$\frac{I}{I_0} = A\sin^2\left(\frac{\pi d \Delta n}{\lambda}\right) \quad (2)$$

$$R = d \times \Delta n \quad (3)$$

$$\Delta n = a + \frac{b}{\lambda^2} + \frac{c}{\lambda^4} + \frac{d}{\lambda^4} \quad (4)$$

2. Measurement of DSC

DSC was measured under a nitrogen atmosphere at a heating and cooling rate of 10° C./min using DSC7 manufactured by Perkin-Elmer.

3. Polarizing Microscope Observation (Determination of Liquid Crystalline Phase Behavior)

The liquid crystal phase behavior together with the results of the measured DSC was examined with a polarizing microscope (model BX50) manufactured by OLYMPUS CORPORATION equipped with a hot stage FP82 manufactured by Mettler-Toledo International Inc. with a thermostat that is an FP90 central processor manufactured by Mettler-Toledo International Inc.

Cr, S, N and Iso indicate crystal phase, smectic phase, nematic phase and isotropic phase, respectively.

4. Measurement of NMR Spectrum

A sample was dissolved in a deuterated chloroform, deuterated dimethyl formamide or deuterated dimethylsulfoxide solvent using tetramethylsilane (TMS) as an internal standard so as to measure the $^1$H- and/or $^{13}$C-NMR spectrum with an NMR device (JEOL LNM-EX400).

5. Measurement of Molecular Weight

The molecular weight was measured at 25° C., flowing a THF solvent (flow rate: 1 ml/min) with a gel permeation chromatograph equipped with JASCO UV-2070 and JASCO RI-2031 detectors, on which a separation column that is TOSOH TSKgel G3000HXL or G4000HXL was set. Polystyrene was used as a standard for calibration of the molecular weight.

6. The Following Devices were Used as Needed

FT-IR: JASCO FT-IR 460 plus a spectrometer

UV-vis spectrum: Beckman Coutler DU800 UV-vis Spectrometer

High resolution mass spectrum: JEOL JMS700 mass spectrometer

Example 1

Synthesis of 1,4-bis(4-butylbenzo[b]thiophenyl-5-yl)buta-1,3-diyne

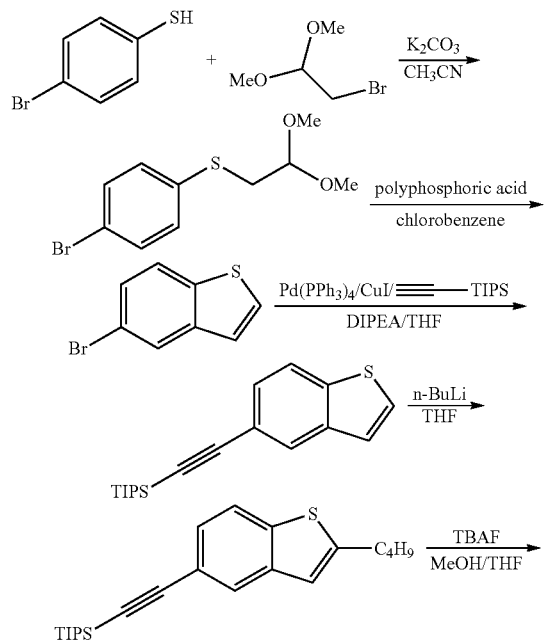

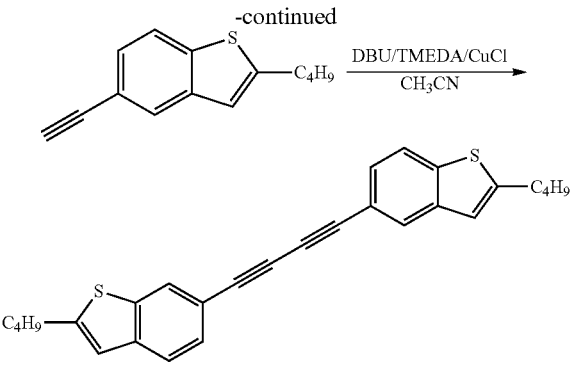

(Abbreviations)
n-BuLi n-butyllithium
DBU 1,8-diazabicyclo[5.4.0]undeca-7-ene
DIPEA diisopropylethylamine
MeOH methanol
Ph phenyl group
TBAF tetrabutylammonium fluoride
THF tetrahydrofuran
TIPS triisopropylsilyl group
TMEDA N,N,N',N'-tetramethylethylene diamine (1) Synthesis of
1-bromo-4-(2,2-dimethoxyethyl-sulfenyl)benzene NaH (1.2 g, 20.5 mmol, 60% in mineral oil) was added to a dry THF (20 ml) solution of 4-bromobenzene thiol (3.0 g, 15.8 mmol) and reacted at room temperature for 10 minutes. Next, bromoacetaldehyde dimethyl acetal (2.8 mL, 23.7 mmol) was added to the mixture and reacted while being refluxed for two days.

After the solvent was removed to extract the residue with diethyl ether and the residue was washed with water and dried with MgSO$_4$, the ether was evaporated. Thereafter, the residue was treated with a silica gel column chromatography (eluate: acetic acid ethyl/hexane=1/10) thereby producing an intended product (4.9 g, yield: 99%).

[Spectrum Data]

$^1$H-NMR (CDCl$_3$, ppm): δ 7.40 (d, J=8.28 Hz, 2H), 7.25 (d, J=8.52 Hz, 2H), 4.51 (t, J=5.5 Hz, 1H), 3.36 (s, 6H), 3.09 (d, J=5.6 Hz, 2H).

(2) Synthesis of 5-bromobenzo[b]thiophene

A mixture of polyphosphoric acid (5.0 g) and chlorobenzene (100 mL) was refluxed for three hours, and then to the mixture was added 1-bromo-4-(2,2-dimethoxyethyl-sulfenyl)benzene (2.50 g, 9.00 mmol). The reaction mixture was stirred at 180° C. for two days.

After the solvent was removed to extract the residue with diethyl ether and the organic layer was washed with a sodium hydrogen carbonate aqueous solution and dried with MgSO$_4$, the ether was evaporated and the residue was treated with a silica gel column chromatography (eluate: hexane) thereby producing an intended product (1.15 g, yield: 60%).

[Spectrum Data]

$^1$H-NMR (CDCl$_3$, ppm): δ 7.97 (d, J=1.72 Hz, 1H), 7.74 (d, J=8.56 Hz, 1H), 7.48 (d, J=5.4 Hz, 1H), 7.44 (dd, J1=8.52 and 1.96 Hz, 1H), 7.28 (s, 1H).

(3) Synthesis of 5-(2-triisopropylsilyl)benzo[b]thiophene (Sonogashira Coupling)

Sonogashira coupling reaction was carried out using 5-bromobenzo[b]thiophene (1.1 g, 5.3 mmol), triisopropylsilyl acetylene (2.2 ml, 9.6 mmol), N-diisopropylethylamine (10 ml), THF (20 ml), Pd(PPh$_3$)$_4$ (0.31 g, 0.27 mmol), CuI (51 mg, 0.27 mmol) and PPh$_3$ (70 mg, 0.27 mmol).

The resulting product was treated in accordance with a conventional method thereby producing an intended product (1.3 g, yield: 78%).

[Spectrum Data]
$^1$H-NMR (400 MHz, CDCl$_3$, ppm): δ 7.96 (d, J=0.96 Hz, 1H), 7.80 (d, J=8.56 Hz, 1H), 7.89-7.42 (m, J=9.52 Hz, 1H), 7.30 (dd, J=9.4 and 0.72 Hz, 1H), 1.15 (s, 21H).

(4) Synthesis of 2-butyl-5-(2-triisopropylsilyl)benzo[b]thiophene

An n-BuLi (0.73 mL, 2.6 M/L, 1.9 mmol)/n-hexane solution was added dropwise to a 5-(2-triisopropylsilyl)benzo[b]thiophene (0.50 g, 1.6 mmol)/THF (30 mL) solution having been cooled to −78° C. At the same temperature, the mixture was reacted for one hour, followed by addition of 1-iodinebutane (0.27 ml, 1.9 mmol). Thereafter, the mixture was heated gradually to room temperature and stirred for 14 hours. The mixture to which water had been added was extract with diethyl ether and then the organic layer was dried with MgSO$_4$ and then concentrated.

The crude product was treated with a silica gel column chromatography (eluate: hexane) thereby producing an intended product (0.48 g, yield: 81%).

[Spectrum Data]
$^1$H-NMR (400 MHz, CDCl$_3$, ppm): δ 7.78 (s, 1H), 7.68-7.66 (m, 1H), 7.35 (dd, J=8.32 and 1.48 Hz, 1H), 6.94 (s, 1H), 2.89 (t, J=6.66 Hz, 2H), 1.46-1.37 (m, 2H), 1.15 (s, 21H), 0.95 (t, J=7.32 Hz, 3H).

(5) Synthesis of 2-butyl-5-ethynylbenzo[b]thiophene

A mixture of 2-butyl-5-(2-triisopropyl silyl)benzo[b]thiophene (0.44 g, 1.2 mmol), tetrabutylammonium fluoride (2.2 ml, 2.2 mmol) and THF (30 ml) was stirred at room temperature for 30 minutes and then the solvent was removed under reduced pressure. The resulting residue was extracted with diethyl ether. After the residue was washed with water and dried with MgSO$_4$, the ether was evaporated.

The crude product was treated with a silica gel column chromatography (eluate: hexane) thereby producing an intended product (0.27 g, yield: 99%).

(6) Synthesis of 1,4-bis(4-butylbenzo[b]thiophenyl-5-yl)buta-1,3-diyne

Glaser coupling reaction was carried out using 2-butyl-5-ethynylbenzo[b]thiophene (0.27 g, 1.2 mmol), DBU (0.19 ml, 1.2 mmol), TMEDA (0.019 ml, 0.12 mmol), CuCl (12 mg, 0.019 mmol) and acetonitrile (20 ml) and the reaction product was treated by a conventional method thereby producing an intended product. The $^1$H-MR spectrum is shown in FIG. 1.

(7) Preparation of Liquid Crystalline Composition

Figure 2:
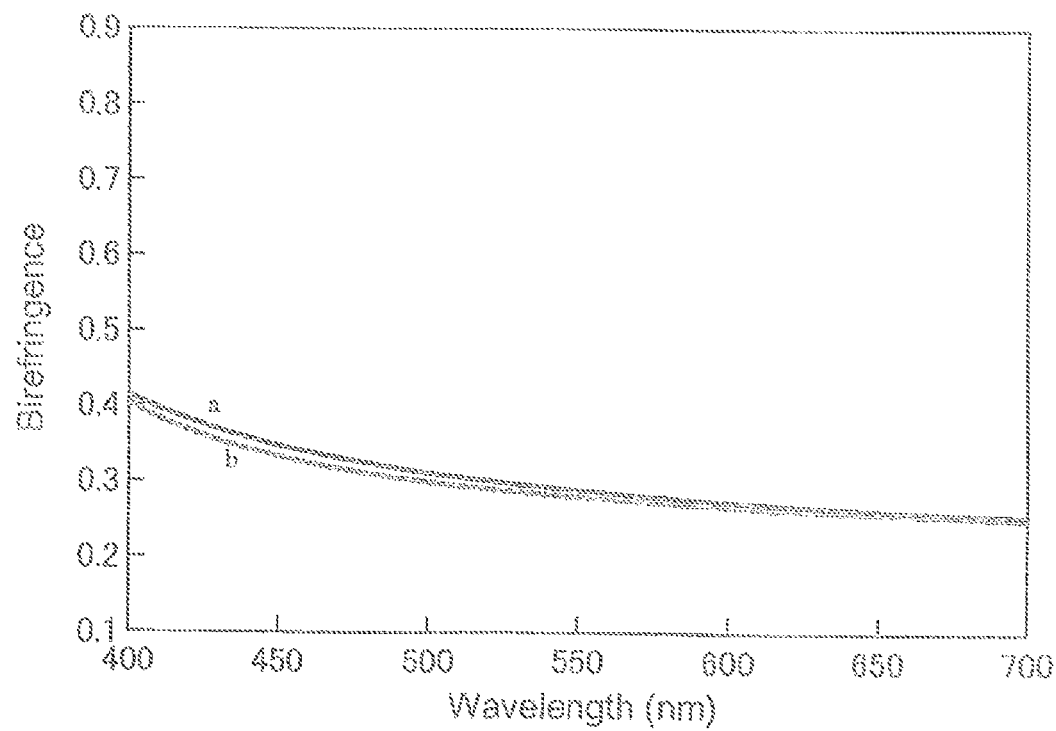
FIG. 2 is a graph showing the wavelength dependence of birefringence of a liquid crystalline composition comprising the diacetylene derivative produced in Example 1 and (4-hexyloxyphenyl-1-yl)buta-1,3-diyne, wherein the lines a and b indicate the birefringences of the composition and (4-hexyloxy)phenyl-1-yl)buta-1,3-diyne, respectively.

A liquid crystalline composition was prepared, which comprises 50 percent by mass of the above-produced 1,4-bis(4-butylbenzo[b]thiophenyl-5-yl)buta-1,3-diyne and 50 percent by mass of the above-produced 1,4-bis(4-hexyloxyphenyl-1-yl)buta-1,3-diyne so as to measure the birefringence. The results are shown in FIG. 2.

The liquid crystal phase behavior of 1,4-bis(4-hexyloxyphenyl-1-yl)buta-1,3-diyne alone was as follows:

Cr, 115.3° C.; N, 147.5° C.; Iso.

Example 2

Synthesis of 1,4-bis(5-hexyl-thieno[3,2-b]thiophenyl-2-yl)buta-1,3-diyne

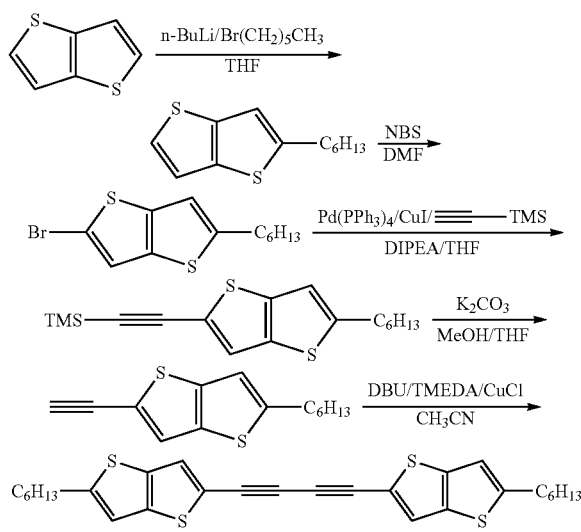

(Abbreviations)
n-BuLi n-butyllithium
DBU 1,8-diazabicyclo[5.4.0]undeca-7-ene
DIPEA diisopropylethylamine
DMF dimethylformamide
NeOH methanol
NBS N-bromosuccinic acid imide
Ph phenyl group
TBAF tetrabutylammonium fluoride
THF tetrahydrofuran
TMEDA N,N,N',N'-tetramethylethylene diamine
TMS trimethylsilyl group

(1) Synthesis of 2-hexyl-thieno[3,2-b]thiophene

An n-BuLi (2.58 ml, 2.6 M/L, 6.72 mmol)/n-hexane solution was added dropwise at −78° C. to a thieno[3,2-]thiophene (0.90 g, 6.40 mmol)/THF (30 mL) solution and reacted for one hour, followed by addition of 1-bromohexane (1.07 ml, 7.68 mmol) at the same temperature. The mixture was gradually cooled down to room temperature and further reacted for two hours. After the mixture was extracted with diethyl ether and the ether layer was washed with water and dried with MgSO$_4$, the solvent was removed under reduced pressure.

The resulting crude product was treated with a silica gel column chromatography (eluate: hexane) thereby producing an intended product (0.80 g, yield: 56%).

[Spectrum Data]
$^1$H-NMR (400 MHz, CDCl$_3$, ppm): δ 7.26 (d, J=5.12 Hz, 1H), 7.18 (d, J=5.12 Hz, 1H), 6.95 (s, 1H), 2.87 (t, J=7.70 Hz, 2H), 1.71 (quip, J=7.57 Hz, 2H), 1.43-1.27 (m, 6H), 0.89 (t, J=7.08 Hz, 3H).

(2) Synthesis of 2-bromo-5-hexyl-thieno[3,2-b]thiophene

Under a light shielded condition, an NBS (0.70 g, 3.92 mmol)/DMF (20 mL) solution was added dropwise at 0° C. to a 2-hexyl-thieno[3,2-b]thiophene (0.80 g, 3.56 mmol)/DMF (5 ml) solution and reacted for 3 hours. After the reaction mixture was extracted with diethyl ether and the organic layer was washed with water and dried with MgSO$_4$, the solvent was removed.

The resulting crude product was treated with a silica gel column chromatography (eluate: hexane) thereby producing an intended product (1.03 g, yield: 96%).

[Spectrum Data]
$^1$H-NMR (400 MHz, CDCl$_3$, ppm): δ 7.17 (s, 1H), 6.85 (s, 1H), 2.84 (t, J=7.68 Hz, 2H), 1.69 (quip, J=7.38 Hz, 2H), 1.43-1.24 (m, 6H), 0.89 (t, J=6.96 Hz, 3H).

(3) Synthesis of 2-(2'-trimethylsilylethynyl)-5-thieno[3,2-b]thiophene

Sonogashira cross coupling reaction was carried out for 2-bromo-5-hexyl-thieno[3,2-b]thiophene (0.30 g, 0.99 mmol), trimethylsilylacetylene (0.21 ml, 0.58 mmol), N-diisopropylethylamine (2 ml), Pd(PPh$_3$)$_4$ (57 mg, 0.050 mmol), CuI (9.4 mg, 0.050 mmol) and PPh$_3$ (13 mg, 0.050 mmol) in THF (5 ml) and the reaction product was treated in accordance with a conventional method thereby producing an intended product (yield: 99%).

[Spectrum Data]
$^1$H-NMR (400 MHz, CDCl$_3$, ppm): δ 7.30 (d, J=0.72 Hz, 1H), 6.87 (d, J=0.72 Hz, 1H), 2.87 (t, J=7.56 Hz, 2H), 1.70 (quin, J=7.56 Hz, 2H), 1.43-1.24 (m, 6H), 0.89 (t, J=7.06 Hz, 3H), 0.25 (s, 9H).

(4) Synthesis of 2-ethynyl-5-hexyl-thieno[3,2-b]thiophene

A mixture of 2-(2-trimethylsilylethynyl)-5-hexyl-thieno[3,2-b]thiophene (0.33 g, 1.03 mmol), potassium carbonate (0.71 g, 5.10 mmol), THF (20 ml) and MeOH (20 ml) were reacted at room temperature for four hours, followed by removal of the solvent under reduced pressure.

After the residue was extracted with diethyl ether and the organic layer was washed with water and dried with MgSO$_4$, the solvent was removed under reduced pressure thereby producing a crude product. The crude product was treated with a silica gel column chromatography (eluate: hexane) thereby producing an intended product (0.20 g, yield: 780).

[Spectrum Data]
$^1$H-NMR (400 Hz, CDCl$_3$, ppm): δ 7.35 (s, 1H), 6.88 (s, 1H), 3.40 (s, 1H), 2.87 (t, J=7.56 Hz, 2H), 1.70 (quin, J=7.51 Hz, 2H), 1.44-1.27 (m, 6H), 0.89 (t, J=7.08 Hz, 3H).

(5) Synthesis of 1,4-bis(5-hexyl-thieno[3,2-b]thiophenyl-2-yl) buta-1,3-diyne Glaser coupling reaction was carried out for 2-ethynyl-5-hexyl-thieno[3,2-b]thiophene (0.19 g, 0.76 mmol), DBU (0.11 ml, 0.76 mmol), TMEDA (0.011 ml, 0.076 mmol), CuCl (9.1 mg, 0.092 mmol) in acetonitrile (20 ml), and the reaction product was treated in accordance with a conventional method thereby producing an intended product (yield: 99%).

As the result of the DSC measurement, the liquid crystal phase behaviors were found to be as follows:

Cr, 103° C.; N, 175° C.; Iso.

(6) Preparation of Liquid Crystalline Composition

Figure 3:
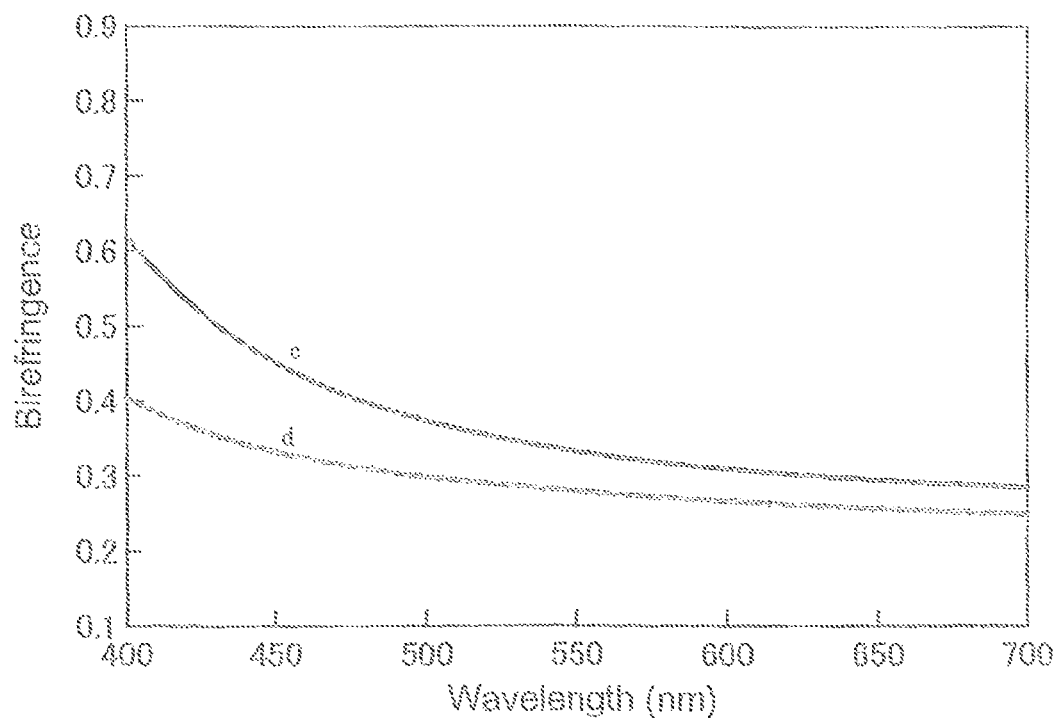
FIG. 3 is a graph showing the wavelength dependence of birefringence of the liquid crystalline composition comprising the diacetylene derivative and (4-hexyloxyphenyl-1-yl)buta-1,3-diyn produced in Example 2, wherein the lines c and d indicate the birefringences of the composition and (4-hexyloxyphenyl-1-yl)buta-1,3-diyne, respectively.

A liquid crystalline composition was prepared from 50 percent by mass of the above-produced 1,4-bis(5-hexyl-thieno[3,2-b]thiophenyl-2-yl)buta-1,3-diyne and 50 percent by mass of the above-produced 1,4-bis(4-hexyloxyphenyl-1-yl)buta-1,3-diyne so as to measure the birefringence. The results are shown in FIG. 3.

Example 3

Synthesis of 1,4-bis(2-hexyloxypyridinyl-5-yl)buta-1,3-diyne

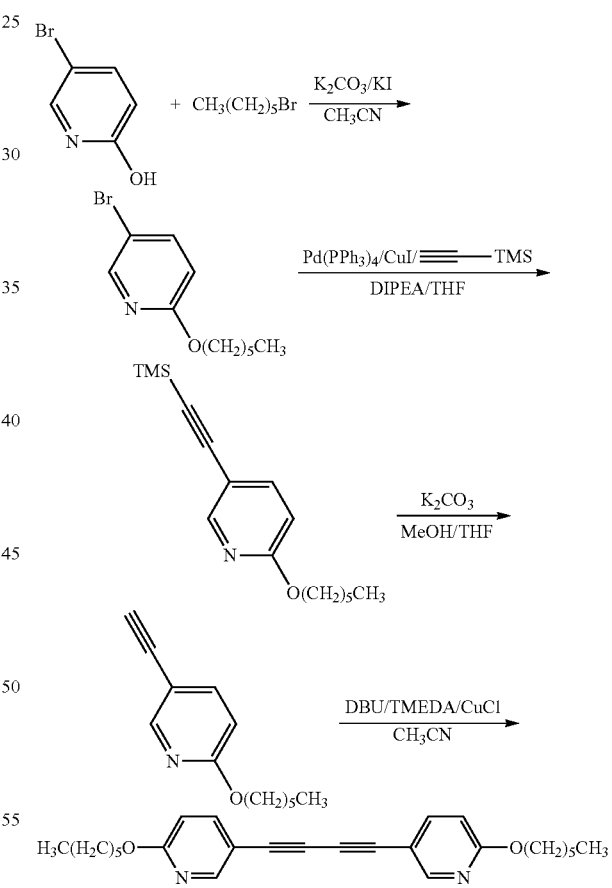

(Abbreviations)
DBU 1,8-diazabicyclo[5.4.0]undeca-7-ene
DIPEA diisopropylethyl amine
NeOH methanol
Ph phenyl group
THF tetrahydrofuran
TMEDA N,N,N',N'-tetramethylethylene diamine

(1) 5-bromo-2-hexyloxypyridine

A mixture of 2-hydroxypyridine (1.0 g, 5.7 mmol), 1-bromohexane (2.8 g, 17 mmol), potassium carbonate (2.4 g, 17 mmol) and acetonitrile (60 ml) was reacted under reflux for four hours.

The residue resulting from removal of the solvent under reduced pressure was extracted with diethyl ether, and then the organic layer was washed with water and dried with $MgSO_4$.

The crude product resulting from removal of the solvent was treated with a silica gel column chromatography (eluate: acetic acid ethyl/hexane=1/3) thereby producing an intended product (1.0 g, yield: 67%).

[Spectrum Data]
$^1$H-NMR (400 MHz, $CDCl_3$, ppm): δ 7.37 (d, J=2.68 Hz, 1H), 7.32 (dd, J=9.52 and 2.68 Hz, 1H), 6.47 (d, J=9.52 Hz, 1H), 3.88 (t, J=7.44 Hz, 2H), 1.73 (quant, J=7.38 Hz, 2H), 1.38-1.29 (m, 6H), 0.89 (t, J=7.06 Hz, 3H).

(2) Synthesis of 2-hexyloxy-5-(2'-trimethylsilyl)ethynyl pyridine

Sonogashira coupling reaction was carried out using 5-bromo-2-hexyloxy pyridine (0.99 g, 3.8 mmol), trimethylsilyl acetylene (0.95 ml, 6.9 mmol), N-diisopropylethylamine (6.5 ml), THF (10 ml), Pd(PPh$_3$)$_4$ (0.13 g, 0.11 mmol), CuI (22 mg, 0.11 mmol) and PPh$_3$ (30 mg, 0.11 mmol), and the reaction product was treated in accordance with a conventional method thereby producing an intended product (yield: 96%).

[Spectrum Data]
$^1$H-NMR (400 MHz, $CDCl_3$, ppm): δ 7.48 (d, J=2.44 Hz, 1H), 7.31 (dd, J=9.26 and 2.44 Hz, 1H), 6.47 (d, J=9.52 Hz, 1H), 3.88 (t, J=7.44 Hz, 2H), 1.77-1.68 (m, 2H), 1.39-1.28 (m, 6H), 0.88 (t, J=6.58 Hz, 3H).

(3) Synthesis of 5-ethynyl-2-hexyl pyridine

A mixture of 2-hexyloxy-5-(2'-trimethylsilyl)ethynyl pyridine (0.96 g, 3.5 mmol), potassium carbonate (2.4 g, 17.5 mmol), MeOH (30 ml) and THF (30 ml) was stirred at room temperature for two days.

After the residue resulting from removal of the solvent under reduced pressure was extracted with diethyl ether, and the organic layer was washed with water and dried with $MgSO_4$, the solvent was removed.

The resulting crude product was treated with a silica gel column chromatography (eluate: acetic acid ethyl/hexane=1/3) thereby producing an intended product (0.56 g, 79%).

[Spectrum Data]
$^1$H-NMR (400 MHz, $CDCl_3$, ppm): δ 7.51 (d, J=2.44 Hz, 1H), 7.33 (dd, J=9.52 and 2.44 Hz, 1H), 6.50 (d, J=9.58 Hz, 1H), 3.90 (t, J=7.58 Hz, 2H), 3.01 (s, 1H), 1.73 (quant, J=7.44 Hz, 2H), 1.38-1.28 (m, 6H), 0.89 (t, J=6.96 Hz, 3H).

(4) Synthesis of 1,4-bis(2-hexyloxypyridinyl-5-yl)buta-1,3-diyne

Figure 4:
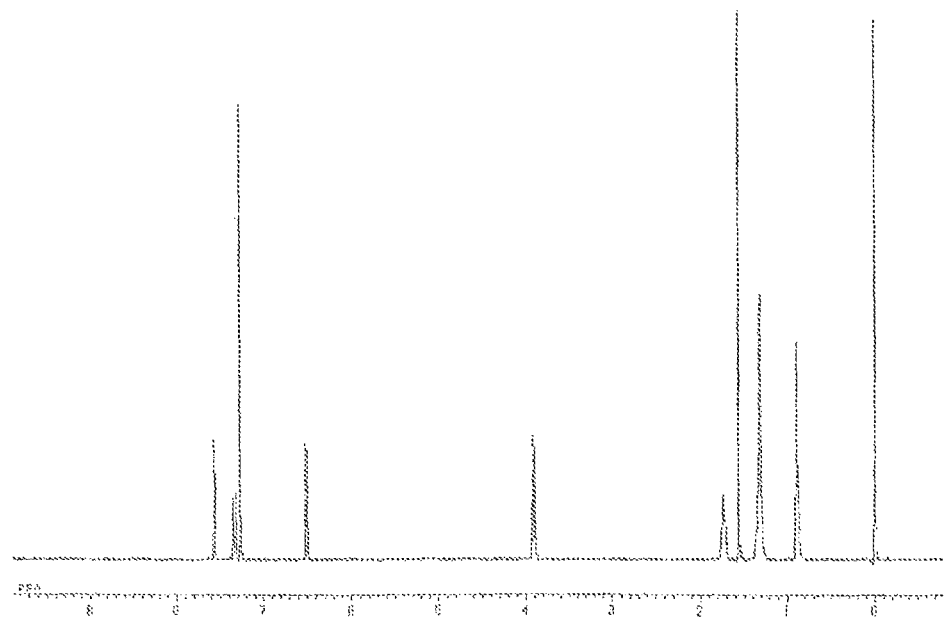
FIG. 4 is a graph showing the $^1$H-NMR spectrum of the diacetylene derivative produced in Example 3.
Figure 5:
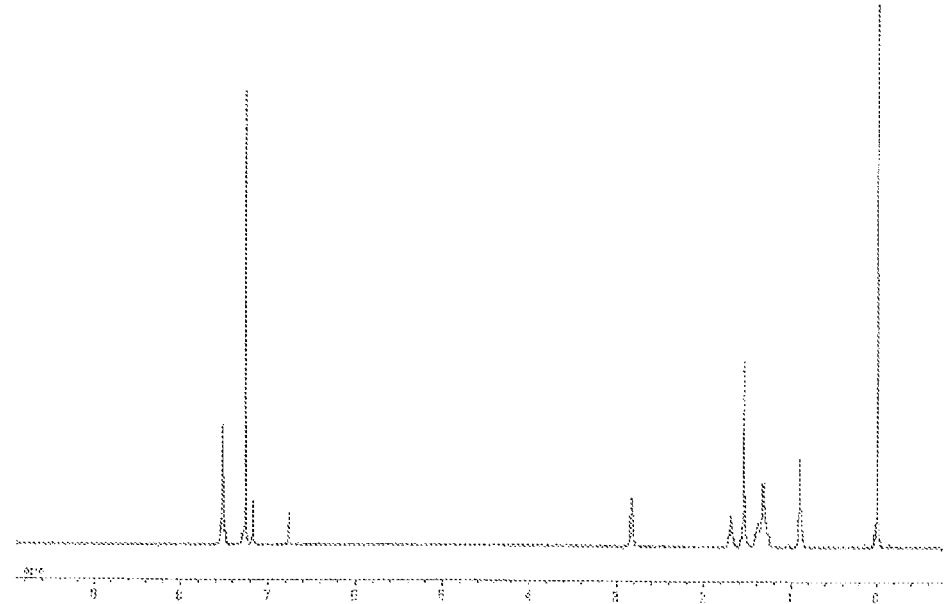
FIG. 5 is a graph showing the $^1$H-NMR spectrum of the diacetylene derivative produced in Example 4.

Glaser coupling reaction was carried out using 5-ethynyl-2-hexyl pyridine (0.56 g, 2.75 mmol), DBU (0.41 ml, 2.75 mmol), TMEDA (41 μmol, 6.2 pml), CuCl (5.5 μmol, 5.4 mg) and acetonitrile (20 ml), and the reactions product was treated in accordance with a conventional method thereby producing an intended product (below). The $^1$H-NMR spectrum is shown in FIG. 4.

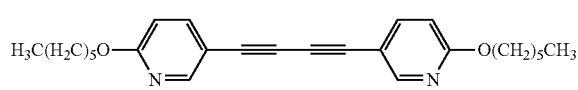

[Spectrum Data]
$^1$H-NMR (400 MHz, $CDCl_3$, ppm): δ 7.56 (d, J=2.44, 1H), 7.33 (dd, J=9.52 and 2.44 Hz, 1H), 6.51 (d, J=9.44 Hz, 1H), 3.90 (t, J=7.44 Hz, 2H), 1.73 (quant, J=7.26 Hz, 2H), 1.38-1.26 (m, 6H), 0.89 (t, J=6.72 Hz, 3H);
$^{13}$C-NMR (100 MHz, $CDCl_3$): δ 161.04, 142.84, 141.14, 121.03, 100.64, 77.63, 74.31, 50.36, 31.33, 29.19, 26.22, 22.44, 13.95

Example 4

Synthesis of 1,4-bis(4-(5-hexylthiophenyl)phenyl-1-yl)buta-1,3-diyne

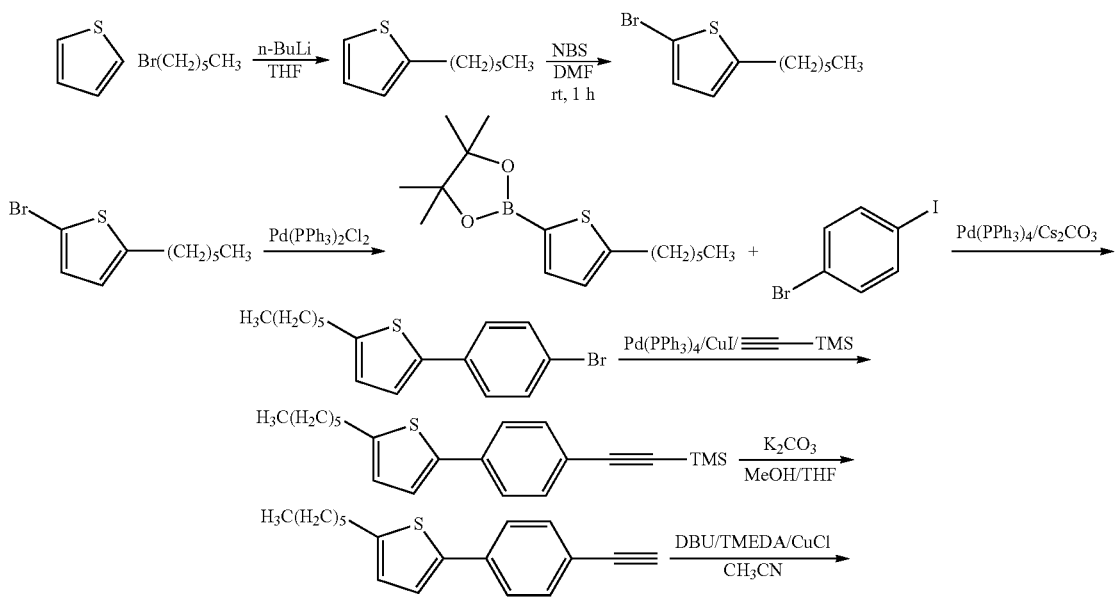

-continued

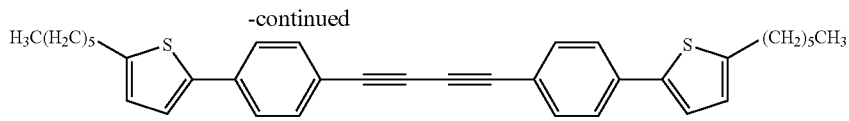

(Abbreviations)
n-BuLi n-butyllithium
DBU 1,8-diazabicyclo[5.4.0]undeca-7-ene
DMF dimethylformamide
MeOH methanol
NBS N-bromosuccinic acid imide
Ph phenyl group
THF tetrahydrofuran
TMEDA N,N,N',N'-tetramethylethylene diamine
TMS trimethylsilyl group (1) Synthesis of 2-hexylthiophene An n-BuLi (8.2 mL, 2.6 M/L, 21.0 mmol) hexane solution was added dropwise at −78° C. to a thiophene (2.0 g, 23.8 mmol)/THF (30 mL) solution and reacted at the same temperature for one hour, and then 1-bromohexane (2.95 mL, 21.0 mmol) was added dropwise thereto. The mixture was gradually heated to room temperature and reacted for 14 hours. After water was added, the mixture was extracted with diethyl ether and, the organic layer was dried with $MgSO_4$ and concentrated.

The resulting crude product was treated with a silica gel column chromatography (eluate: hexane) thereby producing an intended product (3.26 g, yield: 92%).

[Spectrum Data]
$^1$H-NMR (400 MHz, $CDCl_3$, ppm): δ 7.10 (dd, J=5.12 and 1.24, 1H), 6.90 (dd, J=5.12 and 3.4, 1H), 6.78-6.76 (m, 1H), 2.82 (t, J=7.44 Hz, 2H), 1.71-1.62 (m, 2H), 1.40-1.27 (m, 6H), 0.89 (t, J=6.96, 3H).

(2) Synthesis of 2-bromo-5-hexylthiophene

Under a light shielded condition, an NBS (4.11 g, 23.1 mmol)/DMF (30 mL) solution was added dropwise at 0° C. to a 2-hexylthiophene (3.06 g, 18.2 mmol)/DMF (20 mL) solution and reacted at the same temperature for one hour.

After addition of water, the mixture was extracted with diethyl ether and the organic layer was dried with $MgSO_4$, followed by removal of the ether.

The resulting crude product was treated with a silica gel column chromatography (eluate: hexane) thereby producing an intended product (3.97 g, yield: 88%).

[Spectrum Data]
$^1$H-NMR (400 MHz, $CDCl_2$, ppm): δ 6.84 (d, J=3.64 Hz, 1H), 6.52 (d, J=3.68 Hz, 1H), 2.73 (t, J=7.68 Hz, 2H), 1.66-1.54 (m, 2H), 1.38-1.17 (m, 6H), 0.88 (t, J=6.84 Hz, 3H)

(3) Synthesis of 2-(4,4,5,5-tetramethyl-1,3,2-dioxaborane-2-yl)-5-hexylthiophene A mixture of 2-bromo-5-hexylthiophene (1.6 g, 6.3 mmol), 4,4,5,5-tetramethyl-1,3,2-dioxaborane (pinacol borane) (1.4 ml, 9.5 mmol), TEA (2.6 ml, 19 mmol) and dioxane (15 ml) was deaerated with argon, followed by addition of $PdCl_2(PPh_3)_2$ (0.22 g, 0.32 mmol). After the mixture was reacted under reflux for 16 hours, it was extracted with chloroform and the organic layer was dried with $MgSO_4$.

The solvent was removed under reduced pressure, and the resulting crude product was treated with a silica gel column chromatography (eluate: acetic acid ethyl/hexane=1/3) thereby producing an intended product (0.51 g, yield: 93%).

[Spectrum Data]
$^1$H-NMR (400 MHz, $CDCl_3$, ppm): δ 7.47 (d, J=3.40 Hz, 1H), 6.86 (d, J=3.40 Hz, 1H), 2.85 (t, J=7.56 Hz, 2H), 1.68 (quant, J=7.44 Hz, 2H), 1.38-1.24 (m, 18H), 0.88 (t, J=6.60 Hz, 3H)

(4) Synthesis of 2-(4-bromophenyl)-5-hexylthiophene (Suzuki cross coupling)

To a deaerated 2-(4,4,5,5-tetramethyl-1,3,2-dioxaborane-2-yl)-5-hexylthiophene (0.50 g, 1.7 mmol) and THF (15 ml) solution were added 4-bromoiodinebenzene (0.72 g, 2.5 mmol), $Cs_2CO_3$ (1.1 g, 3.4 mmol), $Pd(PPh_3)_4$ (0.06 g, 0.05 mmol) and then the mixture was reacted under reflux for four hours.

After the reaction mixture was extracted with diethyl ether and the organic layer was dried with $MgSO_4$, the solvent was removed under reduced pressure.

The resulting crude product was treated with a silica gel column chromatography (eluate: hexane) thereby producing an intended product (0.51 g, yield: 93%).

[Spectrum Data]
$^1$H-NMR (400 MHz, $CDCl_3$, ppm): δ 7.47-7.41 (m, 4H), 7.11 (d, J=3.64 Hz, 1H), 6.74 (d, J=3.40 Hz, 1H), 2.81 (t, J=7.70 Hz, 2H), 1.69 (quant, J=7.50 Hz, 2H), 1.43-1.28 (m, 6H), 0.89 (t, J=6.70 Hz, 3H)

(5) Synthesis of 2-(4-(2'-trimethylsilyl)ethylphenyl)-5-hexylthiophene (Sonogashira coupling)

Under an argon atmosphere, a mixture of diisopropylethylamine (3 ml), trimethylsilyl acetylene (0.38 ml, 2.8 mmol) and 2-(4-bromophenyl)-5-hexylthiophene (0.50 g, 1.54 mmol) was added to a mixture of $Pd(PPh_3)_4$ (89 mg, 77 μmol), CuI (91 mg, 77 μmol) and $PPh_3$ (20 mg, 77 μmol). The mixture was reacted at 45° C. for one day.

A solution produced by adding diethyl ether to the reaction mixture and removing the insoluble salt by filtration was washed with a hydrochloric acid aqueous solution and water and the organic layer was dried with $MgSO_4$, followed by removal of the solvent under reduced pressure.

The resulting crude product was treated with a silica gel column chromatography (eluate: hexane) thereby producing an intended product (0.35 g, yield: 66%).

(6) Synthesis of 2-(4-ethylphenyl)-5-hexylthiophene

A mixture of 2-(4-(2'-trimethylsilyl)ethylphenyl)-5-hexylthiophene (0.34 g, 1.0 mmol), potassium carbonate (0.71 g, 5.0 mmol), THF (30 ml) and MeOH (30 ml) was stirred at room temperature for two days. After the solvent was removed under reduced pressure and the residue was extracted with diethyl ether, washed with water and dried with $MgSO_4$, it was concentrated under reduced pressure.

The resulting crude product was treated with a silica gel column chromatography (eluate: hexane) thereby producing an intended product (0.29 g, yield: 99%).

(7) Synthesis of 1,4-bis(4-(5-hexylthiophenyl)phenyl-1-yl)buta-1,3-diyne

Oxygen was blown into a mixture of DBU (0.06 ml, 0.41 mmol), TMEDA (0.006 ml, 0.041 mmol), CuCl (0.006 mmol, 4.0 mg) and acetonitrile (15 ml) for five minutes, followed by addition of 2-(4-ethylphenyl)-5-hexylthiophene (0.11 g, 0.41 mmol). The mixture was reacted at room temperature for four hours.

After the solvent was removed under reduced pressure and the residue was extracted with diethyl ether, washed with water and dried with $MgSO_4$, the solvent was removed and the resulting crude product was treated with a silica gel column chromatography (eluate: hexane) and recrystallized thereby producing an intended product (below) (73 mg, 66%).

As the result of the DSC measurement, the liquid crystal phase transition behavior was found to be "Cr, 126° C.; N, 200° C.; Iso".

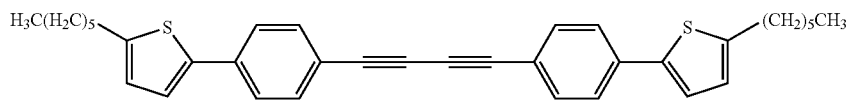

[Spectrum Data]
$^1$H-NMR (400 MHz, $CDCl_3$, ppm): δ 7.52-7.47 (m, 4H), 7.15 (d, J=3.44 Hz, 1H), 6.74 (d, J=3.64 Hz, 1H), 2.81 (t, J=7.58 Hz, 2H), 1.70 (quant, J=7.4 Hz, 2H), 1.43-1.29 (m, 6H), 0.90 (t, J=6.96 Hz, 3H)
$^{13}$C-NMR (100 MHz, $CDCl_3$, ppm): δ 147.04, 140.70, 135.62, 132.97, 125.31, 125.25, 123.68, 120.14, 82.16, 74.88, 31.57, 31.55, 30.33, 28.76, 22.54, 13.98

(8) Preparation of Liquid Crystalline Composition

Figure 6:
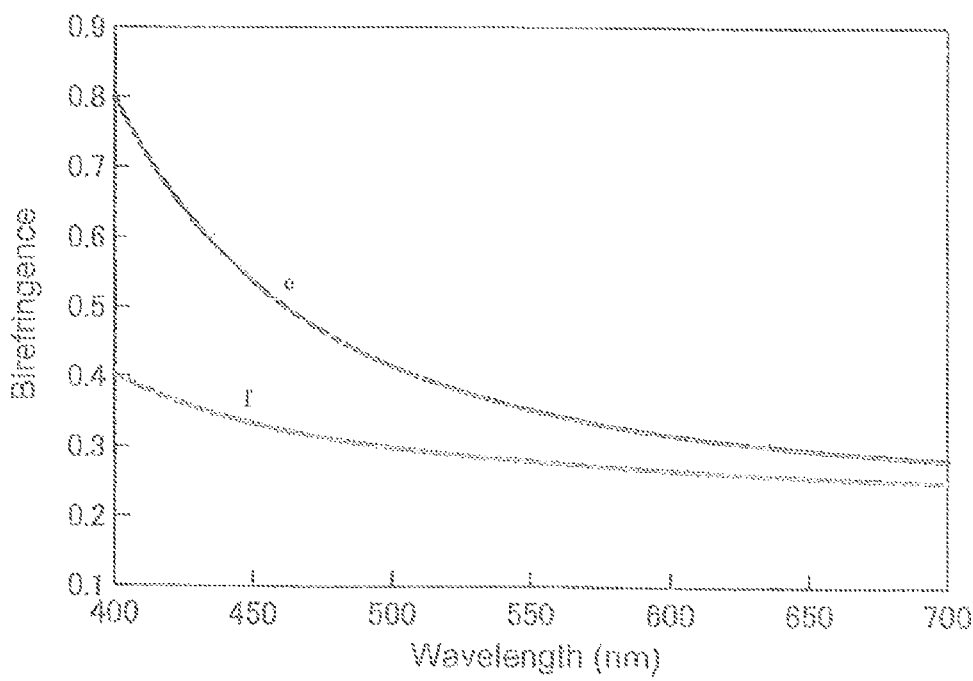
FIG. 6 is a graph showing the wavelength dependence of birefringence of a liquid crystalline composition comprising the diacetylene derivative produced in Example 4 and (4-hexyloxyphenyl-1-yl)buta-1,3-diyne, wherein the lines e and f indicate the birefringences of the composition and (4-hexyloxyphenyl-1-yl)buta-1,3-diyne, respectively.

A liquid crystalline composition was prepared from 50 percent by mass of the above-produced 1,4-bis(4-(5-hexylthiophenyl)phenyl-1-yl)buta-1,3-diyne and 50 percent by mass of the above-produced 1,4-bis(4-hexyloxyphenyl-1-yl)buta-1,3-diyne so as to measure the birefringence. The results are shown in FIG. 6.

Example 5

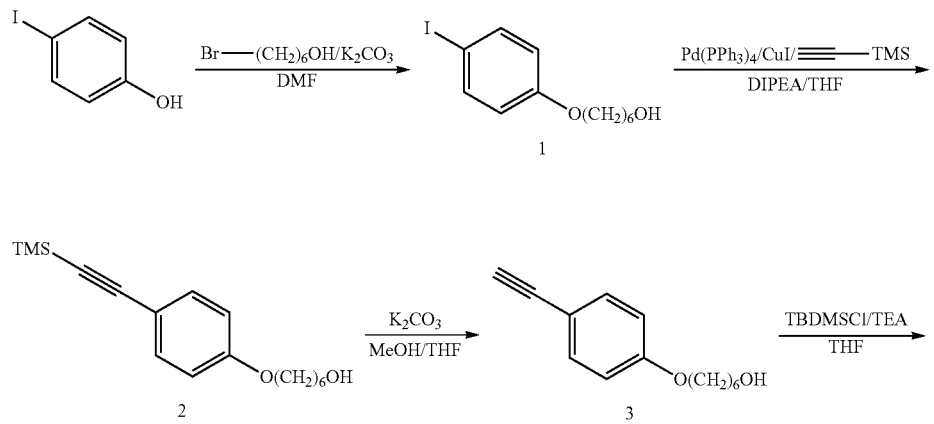

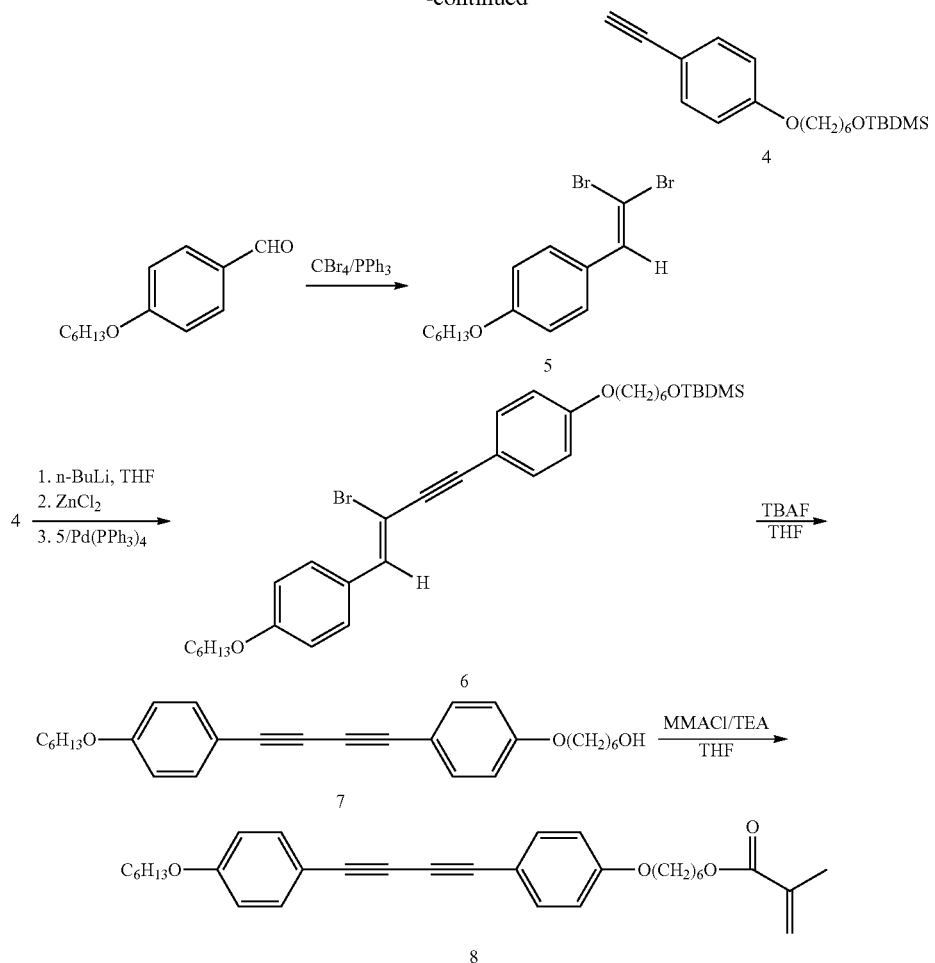

(Abbreviations)
n-BuLi n-butyllithium
DIPEA diisopropylethylamine
DMF dimethylformamide
MeOH methanol,
MMACl methacryloylchloride
Ph phenyl group
TBAF tetrabutylammonium fluoride
TBDMSCl tert-butyldimethylsilyl chloride
TEA triethylamine
THF tetrahydrofuran
TMS trimethylsilyl group (1) Synthesis of Compound 1

A mixture of 4-iodinephenol (5.5 g, 25.1 mmol), 6-bromo-1-hexanol (5.0 g, 27.6 mmol), potassium carbonate (4.2 g, 30.1 mmol) and DMF (50 ml) was reacted at a reflux temperature for 18 hours. After the solvent was removed under reduced pressure and the residue was extracted with diethyl ether and washed with water, the residue was dried with $MgSO_4$ to evaporate the diethyl ether. The residue was treated with a silica gel column chromatography (eluate: acetic acid ethyl/hexane=1/3) thereby producing compound 1 (8.1 g, yield: 99%).

[Spectrum Data]

$^1$H-NMR (400 MHz, $CDCl_3$, ppm): δ 7.54 (d, J=8.52 Hz, 2H), 6.67 (d, J=8.56 Hz, 2H), 3.92 (t, J=6.40 Hz, 2H), 3.67 (q, J=6.01 Hz, 2H), 1.79 (quint, J=6.95 Hz, 2H), 1.64-1.1.36 (m, 6H), 1.26 (s, 1H).

(2) Synthesis of Compound 2

A mixture of TEA (20 ml) deaerated with argon and trimethylsilyl acetylene (5.5 ml, 40 mmol) was added to a mixture of the above-produced compound 1 (8.0 g, 25 mmol), $Pd(PPh_3)_4$ (0.58 g, 0.050 mmol), CuI (95 mg, 0.050 mmol) and $PPh_3$ (0.13 g, 0.050 mmol) and stirred and reacted at 45° C. for two days.

To the reaction mixture was added diethyl ether to remove the insoluble salt by filtration. The resulting product was washed with a hydrochloric acid aqueous solution and water and dried with $MgSO_4$ to evaporate the diethyl ether, and the residue was treated with a silica gel column chromatography (eluate: acetic acid ethyl/hexane=1/2) thereby producing compound 2 (yield: 99%).

[Spectrum Data]

$^1$H-NMR (400 MHz, $CDCl_3$, ppm): δ 7.34 (d, J=8.32 Hz, 2H), 6.80 (d, J=8.08 Hz, 2H), 4.12 (q, J=7.41 Hz, 2H), 3.95 (t, J=6.58 Hz, 2H), 1.82-1.75 (m, 2H), 1.64-1.1.39 (m, 6H), 1.26 (s, 1H).

(3) Synthesis of Compound 3

The resulting compound 2 (3.07 g, 14.1 mmol), TBAF (16 ml, 16 mmol) and THF (50 ml) were stirred for 15 minutes, followed by removal of the solvent under reduced pressure. The residue was extracted with diethyl ether, washed with water, and dried with $MgSO_4$, followed by removal of diethyl ether.

The residue was treated with a silica gel column chromatography (eluate: acetic acid ethyl/hexane=1/3) thereby producing compound 3 (yield with respect to compound 2: 68%).

[Spectrum Data]

$^1$H-NMR (400 MHz, CDCl$_3$, ppm): δ 7.41 (d, J=8.76 Hz, 2H), 6.82 (d, J=8.80 Hz, 2H), 3.96 (t, J=6.52 Hz, 2H), 3.66 (t, J=6.48 Hz, 2H), 2.99 (s, 1H), 1.80 (quint, J=6.89 Hz, 2H), 1.64-1.35 (m, 6H), 1.29 (s, 1H)

(4) Synthesis of Compound 4

Tert-butyl-dimethyl-silylchloride (0.98 g, 6.50 mmol) was added to a solution produced by dissolving compound 3 (1.10 g, 5.00 mmol) and imidazole (0.45 g, 6.50 mmol) in CH$_2$Cl$_2$ (30 mL), followed by stirring at room temperature for three hours. The reaction mixture was extracted with CH$_2$Cl$_2$, washed with water, dried with MgSO$_4$ and then concentrated.

The resulting crude product was treated with a flush column chromatography using silica gel (eluate: acetic acid ethyl/hexane=1/10) thereby producing compound 4 (yield: 99%).

[Spectrum Data]

$^1$H-NMR (400 MHz, CDCl$_3$, ppm): δ 7.41 (d, J=8.56 Hz, 2H), 6.82 (d, J=8.76 Hz, 2H), 3.95 (t, J=6.46 Hz, 2H), 3.61 (t, J=6.48 Hz, 2H), 2.99 (s, 1H), 1.79 (quin, J=6.90 Hz, 2H), 1.56-1.34 (m, 6H), 0.89 (s, 9H), 0.04 (s, 6H)

(5) Synthesis of Compound 5

Tetrabromide carbon (6.6 g, 20 mmol) was added at 0° C. to a CH$_2$Cl$_2$ solution dissolving PPh$_3$ (10.5 g, 40 mmol) and stirred for 15 minutes and then 4-hexyloxybenzaldehyde (2.10 g, 10 mmol) was added thereto. After three hours, methanol was added to terminate the reaction, followed by extraction with chloroform. The organic layer was washed with a sodium thiophosphate aqueous solution and a sodium chloride aqueous solution and dried with MgSO$_4$.

After evaporating the solvent under reduced pressure, the residue was treated with a silica gel column chromatography (eluate: acetic acid ethyl/hexane=1/10) thereby producing compound 5 (1.79 g, yield: 49%).

[Spectrum Data]

$^1$H-NMR (400 MHz, CDCl$_3$, ppm): δ 7.50 (d, J=8.80 Hz, 2H), 7.40 (s, 1H), 6.88 (d, J=7.68 Hz, 2H), 3.96 (t, J=6.58 Hz, 2H), 1.78 (quin, J=7.02 Hz, 2H), 1.49-1.29 (m, 6H), 0.91 (t, 3H).

(6) Synthesis of Compound 6

A solution of compound 4 (1.9 g, 5.7 mmol)/THF (30 mL) was cooled to −78° C. and n-BuLi (2.2 mL, 2.6 M, 5.8 mmol) was added thereto and reacted therewith for 30 minutes. To the reaction mixture was added a solution of anhydrous ZnCl$_2$ (0.79 g, 5.8 mmol)/THF (15 mL) at −78° C. The mixture was kept at the same temperature for 15 minutes and returned to 0° C. over 30 minutes or longer.

A solution produced by adding to the zinc-containing solution compound 5 (2.0 g, 5.7 mmol) was added to Pd(PPh$_3$)$_4$ (0.33 g, 0.28 mmol)/THF (5 mL) and stirred and reacted at 0° C. for two days. An NH$_4$Cl aqueous solution was added to terminate the reaction. The mixture was extracted with diethyl ether, and the organic layer was washed with an NaHCO$_3$ aqueous solution and a saturated sodium chloride aqueous solution and then dried with MgSO$_4$. The residue was concentrated under reduced pressure and treated with a silica gel column chromatography (eluate: acetic acid ethyl/hexane=1/10) thereby producing compound 6.

[Spectrum Data]

$^1$H-NMR (400 MHz, CDCl$_3$, ppm): δ 7.69 (d, J=9.04, 2H), 7.41 (d, J=8.56 Hz, 2H), 7.21 (s, 1H), 6.89 (d, J=8.80 Hz, 2H), 6.85 (d, J=8.76 Hz, 2H), 3.97 (q, J=6.35 Hz, 4H), 3.62 (t, J=6.46 Hz, 2H), 1.86-1.73 (m, 4H), (7) Synthesis of Compound 7

To a solution of compound 6 (1.60 g, 2.60 mmol)/THF (20 ml) was added a 1.0 M/L TBAF/THF solution (4.80 mL, 4.80 mmol) under an argon atmosphere, and the mixture was reacted at room temperature for one day.

The organic layer was extracted with chloroform and washed with water, followed by drying with MgSO$_4$. The solvent was removed, and the residue was treated with a silica gel column chromatography (eluate: chloroform/acetic acid ethyl/hexane=1/1/1) thereby producing compound 7 (1.05 g).

[Spectrum Data]

$^1$H-NMR (400 MHz, CDCl$_3$, ppm): δ 7.44 (d, J=8.80 Hz, 4H), 6.83 (d, J=8.56 Hz, 4H), 3.98-3.94 (m, 4H), 3.70-3.62 (m, 2H), 1.83-1.74 (m, 4H), 1.64-1.33 (m, 12H), 0.90 (t, J=6.84 Hz, 3H).

(8) Synthesis of Compound 8

To a solution of compound 7 (0.97 g, 2.30 mmol) and TEA (3.00 ml, 3.00 mmol)/CH$_2$Cl$_2$ (35 ml) was added methacryloylchloride (0.29 ml, 3.00 mmol), and the mixture was reacted at room temperature for seven hours.

Figure 7:
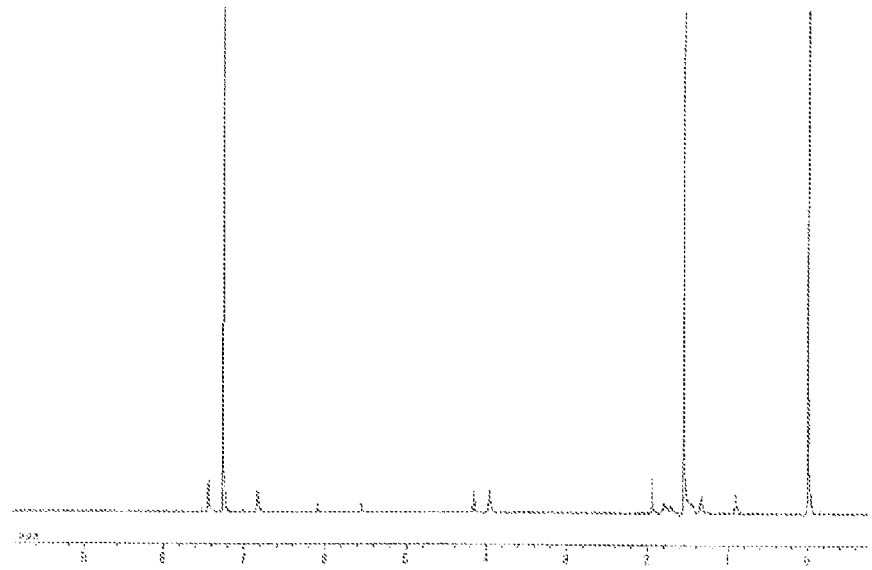
FIG. 7 is a graph showing the $^1$H-NMR spectrum of the diacetylene derivative produced in Example 5.
Figure 8:
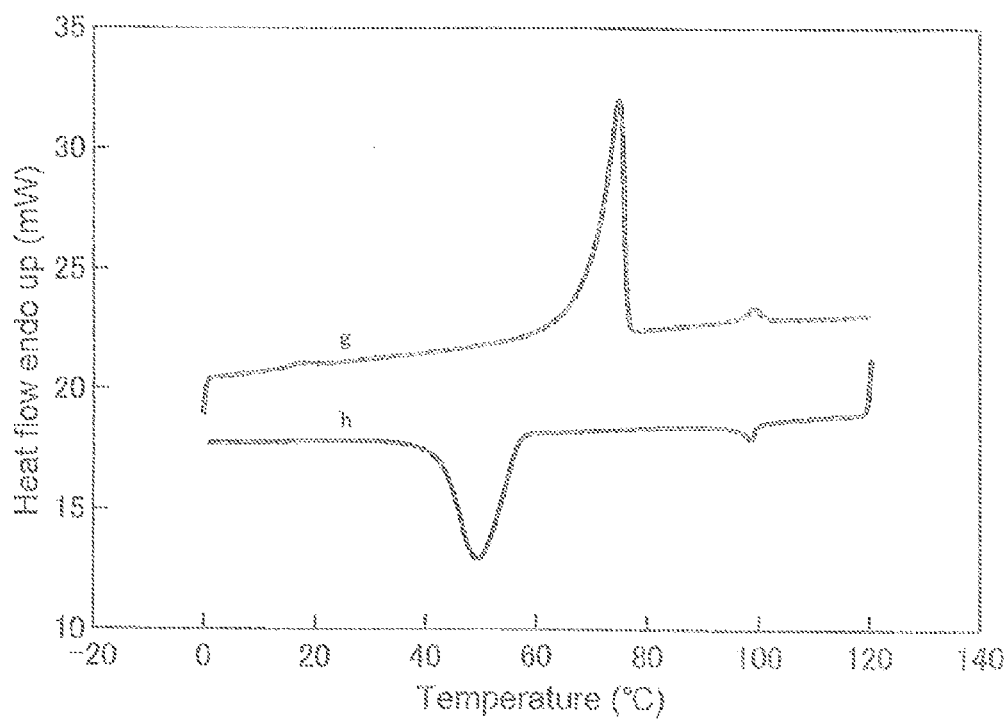
FIG. 8 is a graph showing the results of measurement of DSC of the diacetylene derivative produced in Example 5, wherein the lines g and h indicate the thermal behaviors when the temperature is increased and lowered, respectively.

The reaction mixture was extracted with chloroform, and the organic layer was dried with MgSO$_4$, followed by removal of the solvent. The resulting crude product was treated with a flush column chromatography using silica gel (eluate: acetic acid ethyl/hexane=1/2) thereby producing compound 8 (below). The $^1$H-NMR spectrum and DSC measurement result are shown in FIGS. 7 and 8, respectively.

[Spectrum Data]

$^1$H-NMR (400 MHz, CDCl$_3$, ppm): δ 7.47-7.40 (m, 4H), 6.83 (dd, J=9.04 and 2.44 Hz, 4H), 6.10 (s, 1H), 5.55 (s, 1H), 4.16 (t, J=6.58 Hz, 2H), 3.98-3.94 (m, 4H), 1.94 (s, 3H), 1.82-1.67 (m, 6H), 1.53-1.31 (m, 10H), 0.91 (t, J=6.72 Hz, 3H).

Example 6

Synthesis of 1,4-bis(5'-hexyl-2,2'-bithiophene-5-yl) buta-1,3-diyne

-continued

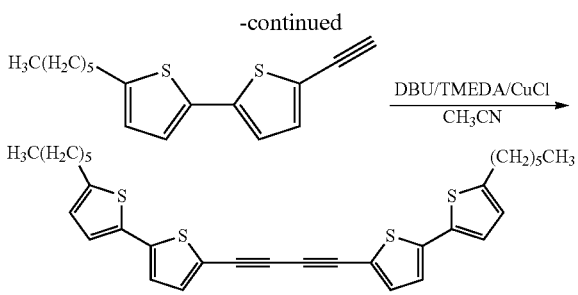

(Abbreviations)
n-BuLi n-butyllithium
DBU 1,8-diazabicyclo[5.4.0]
undeca-7-ene
DIPEA diisopropylethylamine
DMF dimethylformamide
MeOH methanol
NBS N-bromosuccinic acid imide
Ph phenyl group
TBAF tetrabutylammoniumfluoride
THF tetrahydrofuran
TMEDA N,N,N',N'-tetramethylethylene diamine
TMS trimethylsilyl group (1) Synthesis of 5-hexyl-2,2'-bithiophene An n-BuLi (1.30 mL, 2.6 M/L, 3.43 mmol)/n-hexane solution was added dropwise to a 2,2'-bithiophene (0.57 g, 3.43 mmol)/THF (20 ml) solution cooled to −78° C. and reacted at the same temperature for one hour, followed by addition of 1-bromohexane (0.48 ml, 3.43 mmol). The mixture was gradually heated to room temperature and reacted for 12 hours. After addition of water, the mixture was extracted with diethyl ether, and then the organic layer was dried with MgSO$_4$ and concentrated.

The resulting crude product was treated with a silica gel column chromatography (eluate: hexane) thereby producing an intended product (0.78 g, 91%).

[Spectrum Data]
$^1$H-NMR (400 MHz, CDCl$_3$, ppm): δ 7.16-6.63 (m, 5H), 2.80-2.74 (m, 2H), 1.42-1.27 (m, 6H), 0.89 (t, J=6.34 Hz, 3H)

(2) Synthesis of 5-bromo-5'-hexyl-2,2'-bithiophene

Under a light shielded condition, a 5-hexyl-2,2'-bithiophene (0.66 g, 2.63 mmol)/DMF (10 mL) solution was added to NBS (0.56 g, 3.16 mmol) and reacted for one hour. The reaction mixture was then washed with water and was extracted with diethyl ether. The organic layer was dried with MgSO$_4$, and then the solvent was removed.

The resulting crude product was treated with a silica gel column chromatography (eluate: petroleum ether) thereby producing an intended white solid (0.46 g, yield: 53%).

[Spectrum Data]
$^1$H-NMR (400 MHz, CDCl$_3$, ppm): δ 6.93 (d, J=3.68 Hz, 1H), 6.91 (d, J=3.68 Hz, 1H), 6.83 (d, J=3.68 Hz, 1H), 6.66 (d, J=3.68 Hz, 1H), 2.77 (t, J=7.56 Hz, 2H), 1.69-1.63 (m, 2H), 1.41-1.26 (m, 6H), 0.89 (t, J=6.96 Hz, 3H)

(3) Synthesis of 5-hexyl-5'-(2-trimethylsilylethynyl)-2,2'-bithiophene

Sonogashira cross coupling reaction was carried out using 5-bromo-5'-hexyl-2,2'-bithiophene (0.46 g, 1.39 mmol), tri-methylsilyl acetylene (0.35 ml, 3.50 mmol), N-diisopropylethylamine (4.8 ml), Pd(PPh$_3$)$_4$ (80 mg, 0.070 mmol), CuI (13 mg, 0.070 mmol) and THF (10 ml), and the reaction was treated in accordance with a conventional method, thereby producing an intended product (yield: 62%).

[Spectrum Data]
$^1$H-NMR (400 MHz, CDCl$_3$, ppm): δ 7.09 (d, J=3.92 Hz, 1H), 6.98 (d, J=3.44 Hz, 1H), 6.91 (d, J=3.92 Hz, 1H), 6.67 (d, J=3.64 Hz, 1H), 2.78 (t, J=7.56 Hz, 2H), 1.67 (quin, J=7.50 Hz, 2H), 1.42-1.27 (m, 6H), 0.89 (t, J=6.82 Hz, 3H), 0.25 (s, 9H).

(4) Synthesis of 5-ethynyl-5'-hexyl-2,2'-bithiophene

A mixture of 5-hexyl-5'-(2-trimethylsilylethynyl)-2,2'-bithiophene (0.29 g, 0.85 mmol), potassium carbonate (0.66 g, 4.78 mmol), THF (30 ml) and MeOH (30 ml) was reacted for three hours, followed by removal of the solvent. The residue was extracted with diethyl ether, and the organic layer was washed with water and dried with MgSO$_4$, followed by removal of the solvent.

The resulting crude product was treated with a silica gel column chromatography (eluate: hexane) thereby producing an intended product (0.23 g, yield: 99%).

[Spectrum Data]
$^1$H-NMR (400 MHz, CDCl$_3$, ppm): δ 7.15 (d, J=3.88 Hz, 1H), 6.99 (d, J=3.68 Hz, 1H), 6.93 (d, J=3.64 Hz, 1H), 6.68 (d, J=2.92 Hz, 1H), 3.38 (s, 1H), 2.79 (t, J=7.70 Hz, 2H), 1.67 (quant, J=7.38 Hz, 2H), 1.41-1.27 (m, 6H), 0.89 (t, J=6.72 Hz, 3H)

(5) Synthesis of 1,4-bis(5'-hexyl-2,2'-bithiophene-5-yl)buta-1,3-diyne

Glacer coupling reaction was carried out using 5-ethynyl-5'-hexyl-2,2'-bithiophene (0.23 g, 0.83 mmol), DBU (0.12 ml, 0.83 mmol), TMEDA (1.87 μl, 1.24 μmol), CuCl (1.60 mg, 1.66 μmol) and acetonitrile (20 ml), and the reaction product was treated in accordance with a conventional method thereby producing an intended product (yield: 90%).

From the DSC measurement, the liquid crystal phase behavior was found to be as follows:

Cr, 111.2° C.; N, 147.2° C.; Iso.

[Spectrum Data]
$^1$H-NMR (400 MHz, CDCl$_3$, pm): δ 7.21 (d, J=3.68 Hz, 1H), 7.02 (d, J=3.44 Hz, 1H), 6.95 (d, J=3.92 Hz, 1H), 6.69 (d, J=3.16 Hz, 1H), 2.79 (t, J=7.58 Hz, 2H), 1.67 (quin, J=7.38 Hz, 2H), 1.45-1.25 (m, 6H), 0.89 (t, J=6.34 Hz, 3H);

$^{13}$C-NMR (100 MHz, CDCl$_3$, ppm): δ 146.82, 141.21, 135.37, 133.70, 125.03, 124.44, 122.69, 119.56, 78.81, 77.56, 35.51 (35.51), 30.19, 28.72, 22.55, 14.08.

Example 7

Synthesis of 1-(4-hexyloxyphenyl)-4-(4'-hydroxyhexyloxyphenyl)buta-1,3-diyne

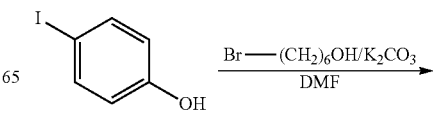

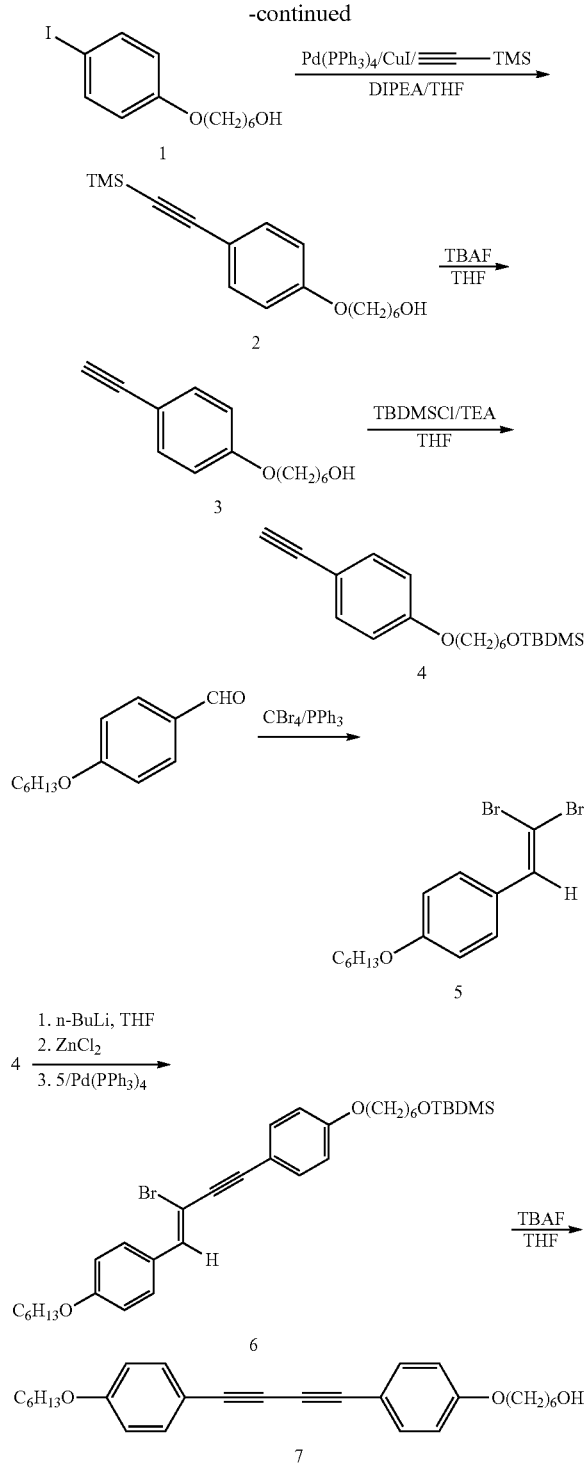

(Abbreviations)
n-BuLi n-butyllithium
DIPEA diisopropylethylamine
DMF dimethylformamide
MeOH methanol
Ph phenyl group
TBAF tetrabutylammoniumfluoride
TBDMS tert-butyldimethylsilyl
TEA triethylamine
THF tetrahydrofuran TMEDA N,N,N',N'-tetramethylethylene diamine
TMS trimethylsilyl group (1) Synthesis of Compound 1

A mixture of 1-iodinephenol (5.5 g, 25.1 mmol), 6-bromo-1-hexanol (5.0 g, 27.6 mmol), potassium carbonate (4.2 g, 30.1 mmol) and DMF (50 ml) was reacted under reflux for 18 hours. The residue resulting from removal of the solvent under reduced pressure was extracted with diethyl ether, and the organic layer was washed with water and dried with $MgSO_4$.

The crude product resulting from removal of the solvent was treated with a silica gel column chromatography (eluate: acetic acid ethyl/hexane=1/3) thereby producing an intended product that is compound (8.1 g, yield: 99%).

[Spectrum Data]
$^1$H-NMR (400 MHz, $CDCl_3$, ppm): δ 7.54 (d, J=8.52 Hz, 2H), 6.67 (d, J=8.56 Hz, 2H), 3.92 (t, J=6.40 Hz, 2H), 3.67 (q, J=6.01 Hz, 2H), 1.79 (quint, J=6.95 Hz, 2H), 1.64-1.1.36 (m, 6H), 1.26 (s, 1H)

(2) Synthesis of Compound 2

TEA (20 ml) and trimethylsilyl acetylene (5.5 ml, 40 mmol) was added under an argon atmosphere to a mixture of compound 1 (8.0 g, 25 mmol), $Pd(PPh_3)_4$ (0.58 g, 0.050 mmol), CuI (95 mg, 0.050 mmol) and $PPh_3$ (0.13 g, 0.050 mmol) and reacted at 45° C. for two days. Diethyl ether was added to the reaction mixture to remove the insoluble salt by filtration, followed by washing with a hydrochloric acid aqueous solution and water and drying with $MgSO_4$.

The crude product resulting from removal of the solvent was treated with a silica gel column chromatography (eluate: acetic acid ethyl/hexane=1/2) thereby producing an intended product that is compound (yield: 99%).

[Spectrum Data]
$^1$H-NMR (400 MHz, $CDCl_3$, ppm): δ 7.34 (d, J=8.32 Hz, 2H), 6.80 (d, J=8.08 Hz, 2H), 4.12 (q, J=7.41 Hz, 2H), 3.95 (t, J=6.58 Hz, 2H), 1.82-1.75 (m, 2H), 1.64-1.1.39 (m, 6H), 1.26 (s, 1H).

(3) Synthesis of Compound 3

A mixture of compound 2 (3.07 g, 14.1 mmol), TBAF (16 ml, 16 mmol) and THF (50 ml) was stirred at room temperature for 15 minutes, followed by removal of the solvent under reduced pressure. The resulting residue was extracted with diethyl ether, and the organic layer was washed with water and dried with $MgSO_4$.

The crude product resulting from removal of solvent was treated with a silica gel column chromatography (eluate: acetic acid ethyl/hexane=1/3) thereby producing an intended product that is compound (yield: 68%).

[Spectrum Data]
$^1$H-NMR (400 MHz, $CDCl_3$, ppm): δ 7.41, (d, J=8.76 Hz, 2H), 6.82 (d, J=8.80 Hz, 2H), 3.96 (t, J=6.52 Hz, 2H), 3.66 (t, J=6.48 Hz, 2H), 2.99 (s, 1H), 1.80 (quint, J=6.89 Hz, 2H), 1.64-1.35 (m, 6H), 1.29 (s, 1H)

(4) Synthesis of Compound 4

Tert-butyl-dimethylsilyl-chloride (0.98 g, 6.50 mmol) was added to a solution of compound 3 (1.10 g, 5.00 mmol), imidazole (0.45 g, 6.50 mmol)/$CH_2Cl_2$ (30 mL) and reacted at room temperature for three hours. The reaction mixture was extracted with $CH_2Cl_2$, and the organic layer was washed with water and dried with $MgSO_4$ and then concentrated.

The resulting crude product was treated with a flush column chromatography using silica gel (eluate: acetic acid ethyl/hexane=1/10) thereby producing an intended product that is compound 4 (yield: 99%).

[Spectrum Data]
$^1$H-NMR (400 MHz, $CDCl_3$, ppm): δ 7.41 (d, J=8.56 Hz, 2H), 6.82 (d, J=8.76 Hz, 2H), 3.95 (t, J=6.46 Hz, 2H), 3.61 (t, J=6.48 Hz, 2H), 2.99 (s, 1H), 1.79 (quin, J=6.90 Hz, 2H), 1.56-1.34 (m, 6H), 0.89 (s, 9H), 0.04 (s, 6H)

(5) Synthesis of Compound 5

Tetrabromidecarbon (6.6 g, 20 mmol) was added to a triphenylphosphine (10.5 g, 40 mmol)/CH$_2$Cl$_2$ solution at 0° C. and stirred for 15 minutes, followed by addition of 4-hexyloxybenzaldehyde (2.10 g, 10 mmol) and reaction for three hours. Methanol was added to terminate the reaction. The reaction mixture was extracted with chloroform and washed with a sodium thiosulfide aqueous solution and a saturated sodium chloride aqueous solution, followed by drying with MgSO$_4$.

The crude product resulting from removal of the solvent was treated with a silica gel column chromatography (eluate: acetic acid ethyl/hexane=1/10) thereby producing an intended product (1.79 g, yield: 49%).

[Spectrum Data]

$^1$H-NMR (400 MHz, CDCl$_2$, ppm): δ 7.50, (d, J=8.80 Hz, 2H), 7.40 (s, 1H), 6.88 (d, J=7.68 Hz, 2H), 3.96 (t, J=6.58 Hz, 2H), 1.78 (quin, J=7.02 Hz, 2H), 1.49-1.29 (m, 6H), 0.91 (t, 3H)

(6) Synthesis of Compound 6

At −78° C., a solution of compound 4 (1.9 g, 5.7 mmol)/THF (30 mL) was added to n-BuLi (2.2 mL, 2.6 M/L, 5.8 mmol) and reacted for 30 minutes. A ZnCl$_2$ (0.79 g, 5.8 mmol)/THF (15 mL) solution was added to the reaction mixture at the same temperature and reacted for 15 minutes. The temperature of the mixture was returned to room temperature over 30 minutes or longer.

A Pd(PPh$_3$)$_4$ (0.33 g, 0.28 mmol)/THF (5 mL) solution was added to a solution produced by adding compound 5 (2.0 g, 5.7 mmol) to the above-produced zinc-containing solution at 0° C. and reacted at 0° C. for two days.

The reaction was terminated by adding an NH$_4$Cl aqueous solution, followed by extraction with diethyl ether. The organic layer was washed with an NaHCO$_3$ aqueous solution and dried with MgSO$_4$.

The crude product resulting from removal of the solvent was treated with a silica gel column chromatography (eluate: acetic acid ethyl/hexane=1/10) thereby producing an intended product that is compound 6.

[Spectrum Data]

$^1$H-NMR (400 MHz, CDCl$_3$, ppm): δ 7.69 (d, J=9.04 Hz, 2H), 7.41 (d, J=8.56 Hz, 2H), 7.21 (s, 1H), 6.89 (d, J=8.80 Hz, 2H), 6.85 (d, J=8.76 Hz, 2H), 3.97 (q, J=6.35 Hz, 4H), 3.62 (t, J=6.46 Hz, 2H), 1.86-1.73 (m, 4H)

(7) Synthesis of Compound 7

A tetra-n-butyl ammonium fluoride (4.80 mL, 4.80 mmol)/THF solution was added to compound 6 (1.60 g, 2.60 mmol)/THF (20 ml) solution and reacted at room temperature for one day. The reaction mixture was extracted with chloroform, and the extracted layer was washed with water and dried with MgSO$_4$.

The crude product resulting from removal of the solvent was treated with a silica gel column chromatography (eluate: chloroform/acetic acid ethyl/hexane=1/1/1) thereby producing an intended product that is compound 7.

[Spectrum Data]

$^1$H-NMR (400 MHz, CDCl$_3$, ppm): δ 7.44 (d, J=8.80 Hz, 4H), 6.83 (d, J=8.56 Hz, 4H), 3.98-3.94 (m, 4H), 3.70-3.62 (m, 2H), 1.83-1.74 (m, 4H), 1.64-1.33 (m, 12H), 0.90 (t, J=6.84 Hz, 3H)

Example 8

Synthesis of 1,4-bis(4-butylthiophenyl-1-yl)buta-1,3-diyne

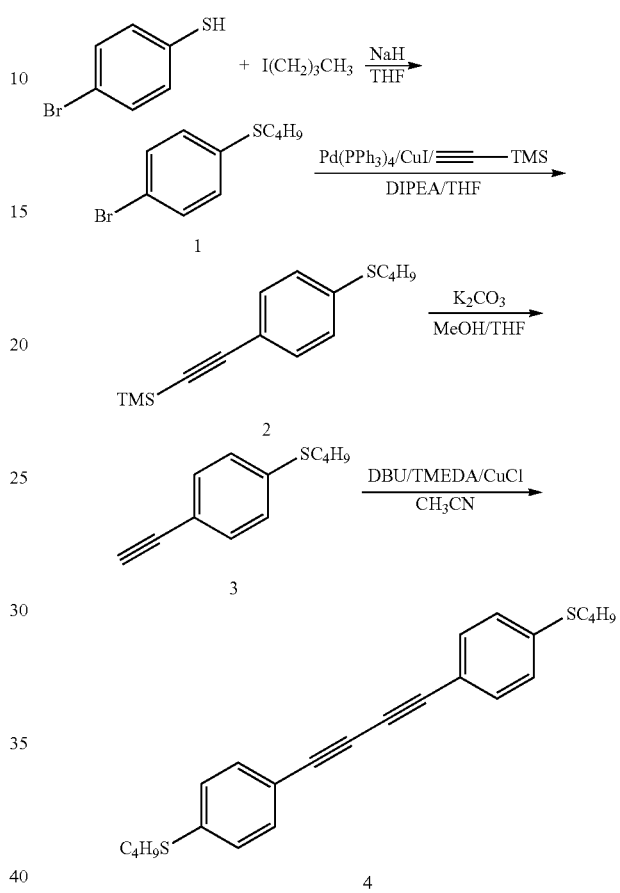

(Abbreviations)
DBU 1,8-diazabicyclo[5.4.0]undeca-7-ene
DIPEA diisopropylethylamine
MeOH methanol
Ph phenyl group
TH tetrahydrofuran
TMEDA N,N,N',N'-tetramethylethylene diamine
TMS trimethylsilyl group (1) Synthesis of Compound 1

A mixture of 4-bromobenzenethiol (0.50 g, 2.64 mmol), sodium hydride (0.21 g, 3.43 mmol) and THF (15 ml) was stirred at room temperature for 10 minutes, followed by addition of 1-iodinebutane (0.45 ml, 4.0 mmol) and reaction under reflux for one day. The solvent was removed under reduced pressure, and the residue was extracted with diethyl ether. The organic layer was washed with water and dried with MgSO$_4$, followed by removal of the solvent. The resulting crude product was treated with a silica gel column chromatography thereby producing an intended product that is compound 1 (yield: 99%).

(2) Synthesis of Compound 2

Into a round-bottom flask having therein a magnetic stirrer and equipped with a reflux condenser and a three-way cock were put Pd(PPh$_3$)$_4$ (0.16 g, 0.14 mmol), CuI (27 mg, 0.14 mmol) and PPh$_3$ (0.37 mg, 0.16 mmol), followed by substitution with argon. To the mixture were added diisopropylethylamine (5 ml), trimethylsilyl acetylene (0.63 ml, 4.6 mmol) and compound 1 (0.70 g, 2.85 mmol), and the mixture was reacted at 45° C. for one day. Diethyl ether was added to remove the insoluble salt thereby producing a solution. The solution was washed with a hydrochloric acid aqueous solution and water.

The organic layer was dried with $MgSO_4$, and the crude product resulting from removal of the solvent was treated with a silica gel column chromatography thereby producing an intended product that is compound 2 (yield: 99%).

(3) Synthesis of Compound 3

A mixture of compound 2 (0.67 g, 2.55 mmol), potassium carbonate (1.77 g, 12.8 mmol), THF (20 ml) and MeOH (20 ml) was stirred at room temperature for 30 minutes. The solvent was removed under reduced pressure, and the residue was extracted with diethyl ether. The organic layer was washed with water and dried with $MgSO_4$, followed by removal of the solvent under reduced pressure. The resulting crude product was treated with a silica gel column chromatography thereby producing an intended product that is compound 3 (yield: 870).

(4) Synthesis of Compound 4

After oxygen was blown into a mixture of DBU (0.31 ml, 2.05 mmol), TMEDA (0.030 ml, 0.20 mmol), CuCl (10 mg, 0.10 mmol) and acetonitrile (20 ml) for five minutes, compound 3 (0.39 g, 2.05 mmol) was added thereto and reacted at room temperature for three hours. The solvent was removed under reduced pressure, and the resulting residue was extracted with diethyl ether. The organic layer was washed with water and dried with $MgSO_4$, followed by removal of the solvent.

The resulting crude product was treated with a silica gel column chromatography, recrystallized with methanol thereby producing an intended product that is compound 4 (yield: 89%).

(5) Preparation of Liquid Crystalline Composition

A liquid crystalline composition was prepared from 50 percent by mass of the above-produced 1,4-bis(4-butylthiophenyl-1-yl) buta-1,3-diyne and 50 percent by mass of the above-produced 1,4-bis(4-hexyloxyphenyl-1-yl) buta-1,3-diyne to measure the birefringence. The results are shown in FIG. 3.

Example 9

Synthesis of Polymer

Under an argon atmosphere, to a 0.5 mol/L THF solution of compound 8 produced in Example 5 was added an n-BuLi solution in an amount of 5 mol % of compound 8, and the mixture was reacted at −10° C. for 24 hours. The polymerization solution was added dropwise to an excess MeOH to allow a polymer to precipitate (below). The polymer was then refined by reprecipitation.

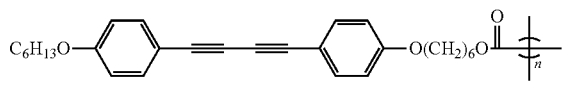

Figure 11:
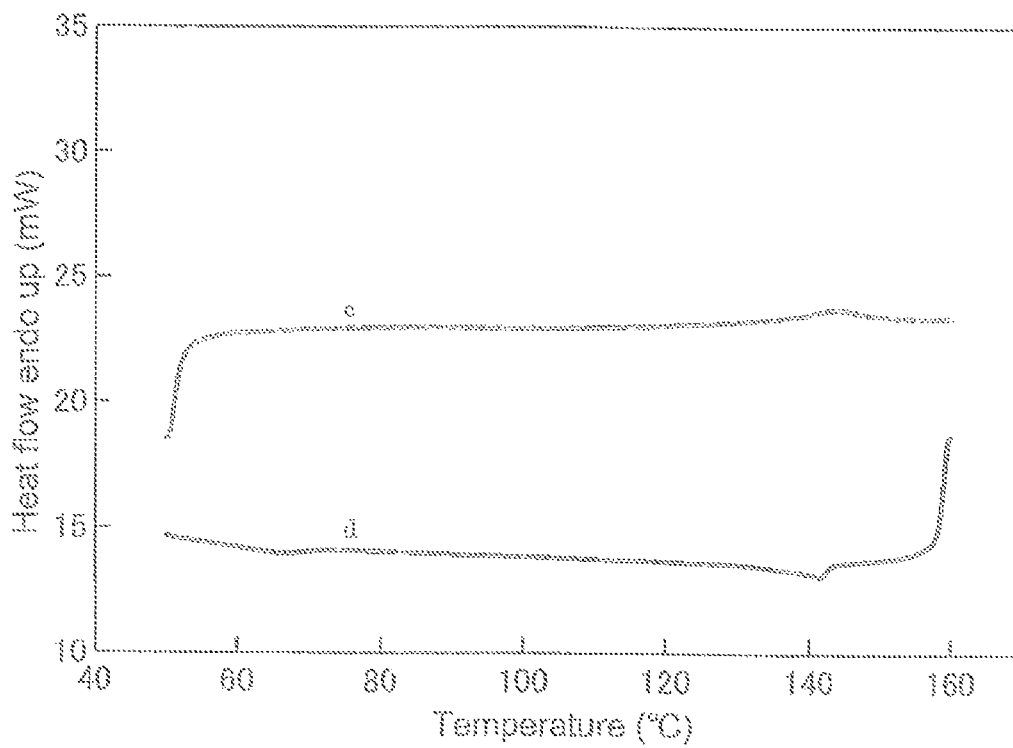
FIG. 11 is a DSC chart of the polymer produced in Example 9, wherein the lines c and d indicate the behaviors when the temperature is increased and lowered, respectively.

The $^1$H-NMR spectrum of the resulting polymer is shown in FIG. 10. The number molecular weight (Mn) of the polymer was 7990 (measured by GPC), and the molecular weight distribution (Mw/Mn) was 1.69. From the results of DSC measurement of the polymer (FIG. 11), the liquid crystalline phase behavior was found to be as follows:

C, 70.3° C.; N, 141.3° C.; I.

Figure 12:
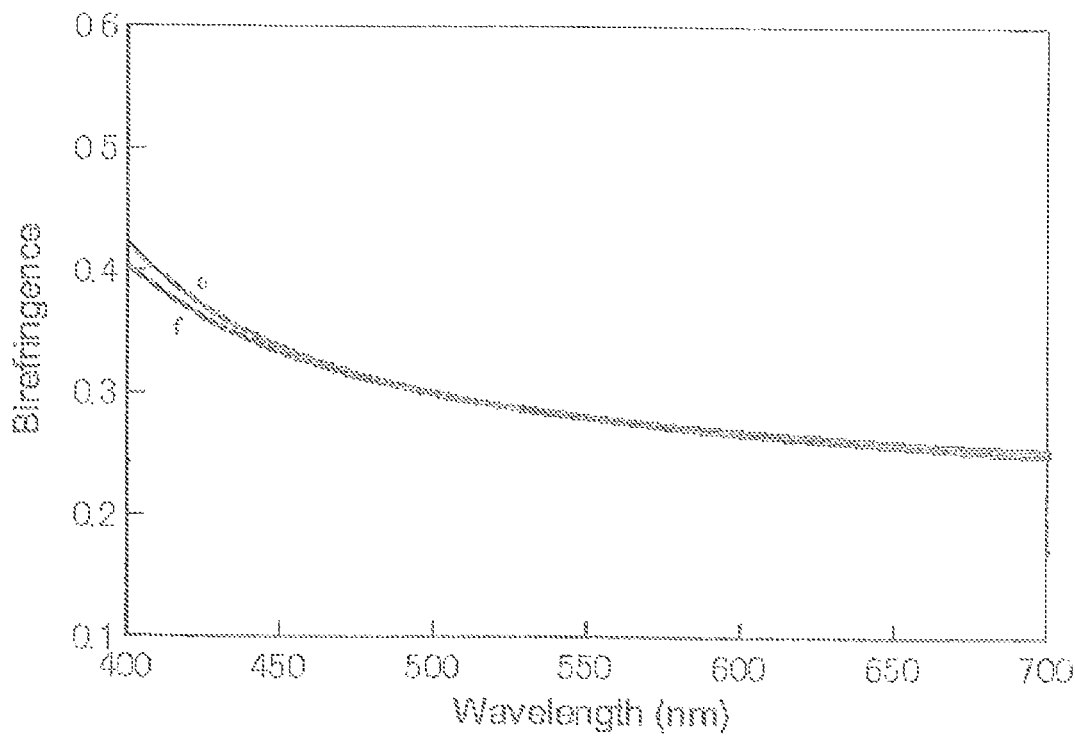
FIG. 12 is a graph showing the wavelength dependence of birefringence of the polymer produced in Example 9, wherein the lines e and f indicate the results of the polymer (at room temperature) and 1,4-bis(4-hexyloxyphenyl)buta-1,3-diyne having a similar structure to the side chain of the polymer at 137.5° C.

A polymer produced by heating the above polymer at an isotropic phase temperature was injected into a cell with a gap of 3 μm and cooled to the glass transition temperature or below at 10° C./min. The optical characteristics (wavelength dependence of birefringence) of the polymer was determined. The results are shown in FIG. 12.

APPLICABILITY IN INDUSTRY

The diacetylene derivative of the present invention exhibits a large refractive index anisotropy, is useful as a material for an electron optical element having excellent performance, as elements constituting a liquid crystal display device, and contributes to an improvement in responsivity. A liquid crystalline polymer having the diacetylene structure of the present invention has a large refractive index anisotropy and is useful as elements constituting various liquid crystal display devices, and can be used for optical or electrooptic purposes due to its easily formability such as into film.

The invention claimed is:

1. A diacetylene derivative represented by the following formula (A)

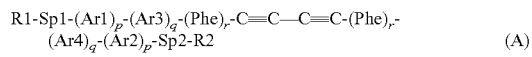

wherein R2 is a reactive group and R1 is hydrogen, halogen, cyano, isothiocyanate, alkyl having 1 to 15 carbon atoms, which is not substituted or is monosubstituted or polysubstituted with halogen, cyano, trifluoromethyl or a reactive group, alkenyl or alkynyl having 2 to 15 carbon atoms, which is not substituted or is monosubstituted or polysubstituted with halogen, cyano, trifluoromethyl or a reactive group, or a reactive group, wherein one or more non-adjacent —CH$_2$— groups may be substituted with —O—, —CO—, —COO— and/or —OCO—; Sp1 and Sp2 are each independently —O—, —S—, —CO—, —COO—, —OCO—, —OCO—O—, —CO—NR3-, —NR3-CO—, —O(CH$_2$)$_n$—, —(CH$_2$)$_n$O—, —CH═CH—COO—, —OCO—CH═CH—, —(CH$_2$)$_m$—, —(SiR4R5-O)$_n$— or a single bond, where m and n are each independently an integer of 1 to 10; R3, R4 and R5 are each independently hydrogen or alkyl having 1 to 4 carbon atoms; Ar1 and Ar2 are each independently an aromatic carbocyclic or heterocyclic group having up to 16 carbon atoms, which is not substituted or is monosubstituted or polysubstituted with halogen, cyano, trifluoromethyl, methyl, ethyl, methoxy or ethoxy and may include a condensed ring; Ar3 and Ar4 are each independently a heterocyclic group having up to 16 carbon atoms, which is not substituted or is monosubstituted or polysubstituted with halogen, cyano, trifluoromethyl, methyl, ethyl, methoxy or ethoxy and may include a condensed ring or be a plurality of heterocyclic groups connected via single bonds; Phe is 1,4-phenylene, which is not substituted or is monosubstituted or polysubstituted with halogen, cyano, trifluoromethyl, methyl, ethyl, methoxy or ethoxy; and p, q and r are each an integer of 0 or 1.

2. A diacetylene derivative represented by formula (1):

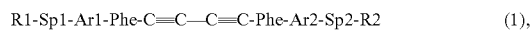

wherein R1 and R2 are each independently hydrogen, halogen, cyano, isothiocyanate, alkyl having 1 to 15 carbon atoms, which is not substituted or is monosubstituted or polysubstituted with halogen, cyano, trifluoromethyl or a reactive group, alkenyl or alkynyl having 2 to 15 carbon atoms, which is not substituted or is monosubstituted or polysubstituted with halogen, cyano, trifluoromethyl or a reactive group, or a reactive group, wherein one or more non-adjacent —CH2- groups may be substituted with —O—, —CO—, —COO— and/or —OCO—; Sp1 and Sp2 are each independently —O—, —S—, —CO—, —COO—, —COO—, —OCO—O—, —CO—NR3-, —NR3-CO—, —O(CH2)n-, —(CH2)nO—, —CH═CH—COO—, —OCO—CH═CH—, —(CH2)m-, —(SiR4R5-O)n- or a single bond, where m and n are each independently an integer of 1 to 10; Ar1 and Ar2 are each independently an aromatic carbocyclic or heterocyclic group having up to 16 carbon atoms, which is not substituted or is monosubstituted or polysubstituted with halogen, cyano, trifluoromethyl, methyl, ethyl, methoxy or ethoxy and may include a condensed ring; and Phe is 1,4-phenylene, which is not substituted or is monosubstituted or polysubstituted with halogen, cyano, trifluoromethyl, methyl, ethyl, methoxy or ethoxy.

3. A The diacetylene derivative represented by formula (2):

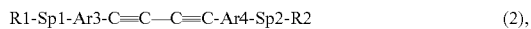  (2), wherein R1 and R2 are each independently hydrogen, halogen, cyano, isothiocyanate, alkyl having 1 to 15 carbon atoms, which is not substituted or is monosubstituted or polysubstituted with halogen, cyano, trifluoromethyl or a reactive group, alkenyl or alkynyl having 2 to 15 carbon atoms, which is not substituted or is monosubstituted or polysubstituted with halogen, cyano, trifluoromethyl or a reactive group, or a reactive group, wherein one or more non-adjacent —CH2- groups may be substituted with —O—, —CO—, —COO— and/or —OCO—; Sp1 and Sp2 are each independently —O—, —S—, —CO—, —COO—, —OCO—, —OCO—O—, —CO—NR3-, —NR3-CO—, —O(CH2)n-, —(CH2)nO—, —CH═CH—COO—, —OCO—CH═CH—, —(CH2)m-, —(SiR4R5-O)n- or a single bond, where m and n are each independently an integer of 1 to 10; and Ar3 and Ar4 are each independently a heterocyclic group having up to 16 carbon atoms, which is not substituted or is monosubstituted or polysubstituted with halogen, cyano, trifluoromethyl, methyl, ethyl, methoxy or ethoxy and may include a condensed ring or be a plurality of heterocyclic groups connected via single bonds.

4. The diacetylene derivative according to claim 1, where the compound represented by formula (A) is a compound represented by formula (3):

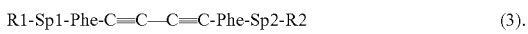  (3).

5. The diacetylene derivative according to claim 1, where the reactive group is hydroxyl, carboxyl, acid anhydride, maleimide, vinyloxy, oxiranyl, oxetanyl, vinyl, (meth)acrylate, or silyl.

6. The diacetylene derivative according to claim 1, where Ar1 and Ar2 are each a furane-2,5-diyl, thiophene-2,5-diyl, pyrrole-2,5-diyl, 1,4-phenylene, naphthalene-2,6-diyl, pyridine-2,5-diyl, pyrimidine-2,5-diyl, or indane-2,5-diyl.

7. The diacetylene derivative according to claim 1, above where Ar3 and Ar4 are each furane-2,5-diyl, thiophene-2,5-diyl, pyrrole-2,5-diyl, pyridine-2,5-diyl, or pyrimidine-2,5-diyl.

8. A liquid crystalline composition containing one or more types of the diacetylene derivative according to claim 1.

9. A liquid crystalline polymer having a diacetylene structure produced by reacting the diacetylene derivative according to claim 1.

10. A liquid crystalline polymer composition containing the liquid crystalline polymer having the diacetylene structure according to claim 9.

11. An optical or electrooptical device comprising the diacetylene derivative according to claim 1.

12. A liquid crystalline display device comprising the diacetylene derivative according to claim 1.

13. An optical or electrooptical device comprising the liquid crystalline polymer according to claim 8.

14. A liquid crystalline display device comprising the liquid crystalline polymer according to claim 8.

* * * * *